(12) United States Patent
Yan et al.

(10) Patent No.: US 8,853,198 B2
(45) Date of Patent: Oct. 7, 2014

(54) AGENTS FOR TREATING DISORDERS INVOLVING MODULATION OF RYANODINE RECEPTORS

(71) Applicants: Les Laboratoires Servier, Suresnes Cedex (FR); Armgo Pharma, Inc., Tarrytown, NY (US)

(72) Inventors: Jiaming Yan, New York, NY (US); Sandro Belvedere, New York, NY (US); Yael Webb, Yorktown Heights, NY (US); Marc Bertrand, Saint Jean le Blanc (FR); Nicole Villeneuve, Rueil Malmaison (FR)

(73) Assignees: Les Laboratoires Servier, Suresnes Cedex (FR); ARMGO Pharma, Inc., Tarrytown, NY (US)

( * ) Notice: Subject to any disclaimer, the term of this patent is extended or adjusted under 35 U.S.C. 154(b) by 0 days.

(21) Appl. No.: 14/076,474

(22) Filed: Nov. 11, 2013

(65) Prior Publication Data

US 2014/0088171 A1    Mar. 27, 2014

Related U.S. Application Data

(63) Continuation of application No. 13/865,359, filed on Apr. 18, 2013.

(60) Provisional application No. 61/625,890, filed on Apr. 18, 2012.

(30) Foreign Application Priority Data

May 11, 2012    (EP) .................................... 12167732

(51) Int. Cl.
*A61K 31/554*    (2006.01)
*C07D 281/10*    (2006.01)
*A61K 31/7088*    (2006.01)
*C07D 285/36*    (2006.01)

(52) U.S. Cl.
CPC ........... *A61K 31/554* (2013.01); *A61K 31/7088* (2013.01); *C07D 281/10* (2013.01); *C07D 285/36* (2013.01)
USPC ...................... 514/211.09; 540/552

(58) Field of Classification Search
CPC ............................. C07D 281/10; A61K 31/554
USPC ...................... 514/211.09; 540/552
See application file for complete search history.

(56) References Cited

U.S. PATENT DOCUMENTS

| | | | |
|---|---|---|---|
| 4,990,707 | A | 2/1991 | Mais |
| 5,580,866 | A | 12/1996 | Housley |
| 5,693,636 | A | 12/1997 | Bondinell |
| 7,544,678 | B2 | 6/2009 | Marks |
| 2004/0224368 | A1 | 11/2004 | Marks |

FOREIGN PATENT DOCUMENTS

| | | |
|---|---|---|
| WO | WO9805857 | 2/1998 |
| WO | WO0100185 | 1/2001 |
| WO | WO0208211 | 1/2002 |
| WO | WO0236116 | 5/2002 |
| WO | WO2005094457 | 10/2005 |
| WO | WO2006101495 | 9/2006 |
| WO | WO2007024717 | 3/2007 |
| WO | WO2007127145 | 11/2007 |
| WO | WO2008021432 | 2/2008 |
| WO | WO2008021439 | 2/2008 |
| WO | WO2008060332 | 5/2008 |
| WO | WO2008064264 | 5/2008 |
| WO | WO2009/111463 | 9/2009 |
| WO | WO2012/019071 | 2/2012 |
| WO | WO2012/019076 | 2/2012 |
| WO | WO2012037105 | 3/2012 |

OTHER PUBLICATIONS

Andersson, D. et al. Cell Metabolism 2011:14(2):196-207.
Bellinger et al., Proc. Natl. Acad. Sci. 2008, 105(6):2198-2002.
Bellinger, A. et al. 2009, Nature Medicine, 15:325-330.
Bellinger, A.M., et al., The Journal of Clinical Investigation, 2008, vol. 118, No. 2, 445-453.
Brillantes et al., Cell, 1994, 77, 513-523.
European Search Report for EP12167732, Oct. 15, 2012.
Fauconnier et al., Proc Natl Acad Sci USA, 2011, 108(32): 13258-63.
First Patentability Opinion for EP12167732.2, Nov. 7, 2012.
Hamada, Y. et al., Bioorg. Med. Chem. Lett. 2006; 16:4354-4369.
Herr, R.J. et al., Bioorg. Med. Chem. 2002; 10: 3379-3393.
International Search Report and Written Opinion for PCT/EP2013/057958, Aug. 6, 2013.
Jayaraman, T., et al., 1992. The Journal of Biological Chemistry, vol. 267, No. 14, pp. 9474-9477.
Kaftan, E., et al., Circulation Research 1996, 78: 990-997.
Katritzky, A. R., et al., J. Chem. Soc., 2002, Perkin Trans. 1, 592-598.
Katritzky, A.R., et al., J. Chem. Soc., 2002, Perkin Trans. 2, 1816-1822.
Kendall et al., (Sci Transl Med, 2012, 4(164). p. 164.
Kimura, T. et al. Bioorg. Med. Chem. Lett. 2006, 16: 2380-2386.
Kohara, Y. et al. Bioorg. Med. Chem. Let.. 1995; 5(17): 1903-1908.
Lehnart et al, J Clin Invest. 2008;118(6):2230-2245.
Lehnart SE, et al., Cell 2005;123(1):25-35.
Marx et al., Science, 1998, vol. 281: 818-821.
Marx, et al. Cell, 2000; 101(4):365-376.
Nair, M.D., et al., Indian Journal of Chemistry, 1969, vol. 7, 862-865.
Olesen, P.H., Curr. Opin. Drug Discov. Devel. 2001; 4: 471-8 (abstract).
Patani. G.A. et al., J. Chem. Rev. 1996; 96:3147.
Reiken, S, et al., J. Cell Biol., 2003, vol. 160, No. 6, 919-928.
Reiken, S., et al., Circulation. 2003: 107: 2459-2466.

(Continued)

*Primary Examiner* — Brenda Coleman
(74) *Attorney, Agent, or Firm* — Hueschen and Sage

(57) ABSTRACT

The present invention relates to 1,4-benzothiazepine derivatives and their use to treat conditions, disorders and diseases associated with ryanodine receptors (RyRs) that regulate calcium channel functioning in cells. The invention also discloses pharmaceutical compositions comprising the compounds and uses thereof to treat diseases and conditions associated with RyRs, in particular cardiac, musculoskeletal and central nervous system (CNS) disorders.

29 Claims, 13 Drawing Sheets

(56) References Cited

OTHER PUBLICATIONS

Shan et al., J Clin Invest., 2010. 120(12):4375-87.
Szabo, J., et al., Can. J. Chem., 1987, vol. 65. 175-181.
Szabo, J., et al., Chem. Ber., 1986, 119, 2904-2913.
Wehrens XH et al. Proc. Natl 25 Acad Sci USA. 2006: 103(3):511-518.
Yamada, T., et al., Arthritis & Rheutism, 2009, vol. 60, No. 11, pp. 3280-3289.
Andersson, et al., (Exhibit M) Leaky ryanodine receptors in beta-sarcoglycan deficient mice: a potential common defect in muscular dystrophy, Skeletal Muscle 2:9, 2012.
Blayney, et al., (Exhibit H) Ryanodine receptor-mediated arrhythmias and sudden cardiac death, Pharmacol Ther., 123(2), pp. 151-177, 2009.
Chakroborty, et al., (Exhibit R) Stabilizing ER Ca2+ channel function as an early preventative strategy for Alzheimer's Disease, PLoS One 7,(12) Dec. 2012.
Chen, et al., (Exhibit T) Dantroiene is neuroprotective in Huntington's Disease transgenic mouse model, Molecular Neurodegeneration 6:81, 2011.
Ellison, et al., (Exhibit E) Acute β-adrenergic overload produces myocyte damage through calcium leakage from the ryanodine receptor 2 but spares cardiac stem cells, Journal of Biological Chemistry, Apr. 13, 2007, vol. 282, No. 15, pp. 11397-11409.
Fauconnier, et al., (Exhibit O) Leaky RyR2 trigger ventricular arrhythmias in Duchenrie muscular dystrophy, PNAS Early Edition, Dec. 3, 2009, pp. 1-6.
Huang, et al., (Exhibit C) Analysis of calstabin2 (FKBP12.6)-ryanodine receptor interations: Rescue of heart failure by Calstabin2 in mice, PNAS, Feb. 28, 2006, vol. 103, No. 9, pp. 3456-3461.
Kushnir, et al., (Exhibit B) The Ryanodine receptor in cardiac physiology and disease. Advances in Pharmacology, vol. 59, pp. 1-30, 2010.
Liu, et al., (Exhibit Q) Role of leaky neuronal ryanodine receptors in stress-induced cognitive dysfuntion, Cell 150, 1055-1067, Aug. 31, 2012.
Oki, et al., (Exhibit P) Androgen receptors in muscle fibers induce rapid loss of force but not mass: implications for spinal bulbar muscular atrophy, Muscle Nerve 47: 823-834, 2013.
Oules, et al., (Exhibit S) Ryanodine receptor blockade reduces amyloid-β load and memory impairments in Tg2576 mouse model of Alzheimer Disease, The Journal of Neuroscience, Aug. 22, 2012, 32(34): 11820-11834.
Oyama, et al., (Exhibit J) Arrhythmogenic right ventricular cardiomyopathy in boxer dogs is associated with calstabin2 deficiency, J Vet Cardiol. doi:10, 1016/j.jvc. 2008.04.003, 2008.
Suzuki, et al., (Exhibit U) Calcium leak through ryanodine receptor is involved in neuronal death induced by mutant huntingtin, Biochem. Biophys. Res. Commun. 2012, pp. 1-6.
Wehrens, et al., (Exhibit A) Ryanodine receptors, structure, function and dysfunction in clinical disease. Editors Wehrens and Marks, Springer Science + Business Media, USA, pp. 155-161 & 254-260, 2005.
Wehrens, et al., (Exhibit F) FKBP12.6 deficiency and defective calcium release channel (ryanodine receptor) function linked to exercise-induced sudden cardiac death. Cell. vol. 113, Jun. 27, 2003, pp. 829-840.
Yano, et al., (Exhibit I) FKBP12.6-mediated stabilization of calcium-release channel (ryanodine receptor) as a novel therapeutic strategy against heart failure, Circulation 107, pp. 477-484, 2003.

AGENTS FOR TREATING DISORDERS INVOLVING MODULATION OF RYANODINE RECEPTORS

FIELD OF THE INVENTION

The present invention relates to 1,4-benzothiazepine derivatives and their use to treat disorders and diseases associated with ryanodine receptors (RyRs) that regulate calcium channel functioning in cells. The invention also discloses pharmaceutical compositions comprising these compounds and uses thereof to treat diseases and conditions associated with RyRs, in particular cardiac, skeletal muscular and central nervous system (CNS) disorders.

BACKGROUND OF THE INVENTION

The sarcoplasmic reticulum (SR) is a structure in cells that functions, among other things, as a specialized intracellular calcium ($Ca^{2+}$) store. RyRs are channels in the SR, which open and close to regulate the release of $Ca^{2+}$ from the SR into the intracellular cytoplasm of the cell. Release of $Ca^{2+}$ into the cytoplasm from the SR increases cytoplasmic $Ca^{2+}$ concentration. Open probability of RyRs refers to the likelihood that a RyR is open at any given moment, and therefore capable of releasing $Ca^{2+}$ into the cytoplasm from the SR.

There are three types of RyR, all of which are highly homologous: RyR1, RyR2, and RyR3. RyR1 is found predominantly in skeletal muscle as well as other tissues, RyR2 is found predominantly in the heart as well as other tissues, and RyR3 is found in the brain as well as other tissues. The RyR is a tetramer. Part of the RyR complex is formed by four RyR polypeptides in association with four FK506 binding proteins (FKBPs) (calstabins), specifically FKBP12 (calstabin1) and FKBP12.6 (calstabin2). Calstabin1 binds to RyR1 and RyR3 while calstabin2 binds to RyR2. The calstabins bind to the RyR (one molecule per RyR subunit), stabilize the RyR function, facilitate coupled gating between neighboring RyRs and prevent abnormal activation ($Ca^{2+}$ leak) of the channel by stabilizing the channel's closed state.

Ryanodine Receptor 2 and Cardiac Diseases

In cardiac striated muscle, RyR2 is the major $Ca^{2+}$ release channel required for excitation-contraction (EC) coupling and muscle contraction. During EC coupling, depolarization of the cardiac-muscle cell membrane during phase zero of the action potential activates voltage-gated $Ca^{2+}$ channels. $Ca^{2+}$ influx through the open voltage-gated channels in turn initiates $Ca^{2+}$ release from the SR via RyR2. This process is known as $Ca^{2+}$-induced $Ca^{2+}$ release. The RyR2-mediated $Ca^{2+}$-induced $Ca^{2+}$ release then activates the contractile proteins in the cardiac cell, resulting in cardiac muscle contraction.

Phosphorylation of RyR2 by protein kinase A (PKA) is an important part of the "fight or flight" response that increases cardiac EC coupling gain by augmenting the amount of $Ca^{2+}$ released for a given trigger. This signaling pathway provides a mechanism by which activation of the sympathetic nervous system (SNS), in response to stress, results in increased cardiac output. Phosphorylation of RyR2 by PKA results in partial dissociation of calstabin2 from the channel, which in turn, leads to increased open probability, and increased $Ca^{2+}$ release from the SR into the intracellular cytoplasm.

Heart failure (HF) is characterized by a sustained hyperadrenergic state in which serum catecholamine levels are chronically elevated. One consequence of this chronic hyperadrenergic state is persistent PKA hyperphosphorylation of RyR2, such that 3-4 out of the four Ser2808 in each homotetrameric RyR2 channel are chronically phosphorylated (Marx S O, et al. *Cell*, 2000; 101(4):365-376). In particular, chronic PKA hyperphosphorylation of RyR2 is associated with depletion of the channel-stabilization subunit calstabin2 from the RyR2 channel macromolecular complex. Depletion of calstabin results in a diastolic SR $Ca^{2+}$ "leak" from the RyR complex, which contributes to impaired contractility (Marx et al., 2000). Due to the activation of inward depolarizing currents, this diastolic SR $Ca^{2+}$ "leak" also is associated with fatal cardiac arrhythmias (Lehnart et al, *J Clin Invest*. 2008; 118(6):2230-2245). Indeed, mice engineered with RyR2 lacking the PKA phosphorylation site are protected from HF progression after myocardial infarction (MI) (Wehrens X H et al. *Proc Natl Acad Sci USA*. 2006; 103(3): 511-518). In addition, chronic PKA hyperphosphorylation of RyR2 in HF is associated with remodeling of the RyR2 macromolecular complex that includes depletion of phosphatases (Marx et al. 2000) PP1 and PP2a (impairing dephosphorylation of Ser2808) and the cAMP-specific type 4 phosphodiesterase (PDE4D3) from the RyR2 complex. Depletion of PDE4D3 from the RyR2 complex causes sustained elevation of local cAMP levels (Lehnart S E, et al., *Cell* 2005; 123(1): 25-35). Thus, diastolic SR $Ca^{2+}$ leak contributes to HF progression and arrhythmias. Moreover, a recent report has demonstrated that RyR2-S2808D+/+ (aspartic acid replacing serine 2808) knock-in mice, that mimic constitutive PKA hyperphosphorylation of RyR2, show depletion of calstabin2 and leaky RyR2. RyR2-S2808D+/+ mice develop age-dependent cardiomyopathy, demonstrate elevated RyR2 oxidation and nitrosylation, a reduced SR $Ca^{2+}$ store content, and increased diastolic SR $Ca^{2+}$ leak. After myocardial infarction, RyR2-S2808D+/+ mice exhibit increased mortality compared with WT littermates. Treatment with S107, a 1,4-benzothiazepine derivative that stabilizes RyR2-calstabin2 interactions (WO 2007/024717), inhibited the RyR2-mediated diastolic SR $Ca^{2+}$ leak and reduced HF progression in both WT and RyR2-S2808D+/+ mice (Shan et al., *J Clin Invest*. 2010 Dec. 1; 120(12):4375-87).

Moreover, RyR2 contains about 33 free thiol residues rendering it highly sensitive to the cellular redox state. Cysteine oxidation facilitates RyR opening and SR $Ca^{2+}$ leak. Shan et al, 2010, demonstrated that oxidation and nitrosylation of RyR2 and dissociation of the stabilizing subunit calstabin2 from RyR2 induces SR $Ca^{2+}$ leak.

Catecholaminergic polymorphic ventricular tachycardia (CPVT) is an inherited disorder in individuals with structurally normal hearts. More than 50 distinct RyR2 mutations have been linked to CPVT. CPVT patients experience syncope and sudden cardiac death (SCD) from the toddler to adult ages, and by 35 years of age the mortality is up to 50%. Individuals with CPVT have ventricular arrhythmias when subjected to exercise, but do not develop arrhythmias at rest. CPVT-associated RyR2 mutations result in "leaky" RyR2 channels due to the decreased binding of the calstabin2 subunit (Lehnart et al., 2008). Mice heterozygous for the R2474S mutation in RyR2 (RyR2-R2474S mice) exhibit spontaneous generalized tonic-clonic seizures (which occurred in the absence of cardiac arrhythmias), exercise-induced ventricular arrhythmias, and SCD. Treatment with S107 enhanced the binding of calstabin2 to the mutant RyR2-R2474S channel, inhibited the channel leak, prevented cardiac arrhythmias and raised the seizure threshold (Lehnart et al., 2008).

Ryanodine Receptor 1 and Skeletal Muscle Diseases

Skeletal muscle contraction is activated by SR $Ca^{2+}$ release via RyR1. Depolarization of the transverse (T)-tubule membrane activates the dihydropyridine receptor voltage sensor (Cav1.1) that in turn activates RyR1 channels via a direct protein-protein interaction causing the release of SR $Ca^{2+}$ stores. $Ca^{2+}$ binds to troponin C allowing actin-myosin cross-bridging to occur and sarcomere shortening.

In conditions of prolonged muscular stress (e.g., during marathon running) or in a disease such as heart failure, both of which are characterized by chronic activation of SNS, skeletal muscle function is impaired, possibly due to altered EC coupling. In particular, the amount of $Ca^{2+}$ released from the SR during each contraction of the muscle is reduced, aberrant $Ca^{2+}$ release events can occur, and $Ca^{2+}$ reuptake is slowed (Reiken, S, et al. 2003. *J. Cell Biol.* 160:919-928). These observations suggest that the deleterious effects of chronic activation of the SNS on skeletal muscle might be due, at least in part, to defects in $Ca^{2+}$ signaling.

The RyR1 macromolecular complex consists of a tetramer of the 560-kDa RyR1 subunit that forms a scaffold for proteins that regulate channel function including PKA and the phosphodiesterase 4D3 (PDE4D3), protein phosphatase 1 (PP1) and calstabin1. A-kinase anchor protein (mAKAP) targets PKA and PDE4D3 to RyR1, whereas spinophilin targets PP1 to the channel (Marx et al. 2000; Brillantes et al., *Cell*, 1994, 77, 513-523; Bellinger et al. *J. Clin. Invest.* 2008, 118, 445-53). The catalytic and regulatory subunits of PKA, PP1, and PDE4D3 regulate PKA-mediated phosphorylation of RyR1 at Ser2843 (Ser2844 in the mouse). It has been shown that PKA-mediated phosphorylation of RyR1 at Ser2844 increases the sensitivity of the channel to cytoplasmic $Ca^{2+}$, reduces the binding affinity of calstabin1 for RyR1, and destabilizes the closed state of the channel (Reiken et al., 2003; Marx, S. O. et al., *Science*, 1998, 281:818-821). Calstabin1 concentrations in skeletal muscle are reported to be approximately 200 nM and that PKA phosphorylation of RyR1 reduces the binding affinity of calstabin1 for RyR1 from approximately 100-200 nM to more than 600 nM. Thus, under physiologic conditions, reduction in the binding affinity of calstabin1 for RyR1, resulting from PKA phosphorylation of RyR1 at Ser2843, is sufficient to substantially reduce the amount of calstabin1 present in the RyR1 complex. Chronic PKA hyperphosphorylation of RyR1 at Ser2843 (defined as PKA phosphorylation of 3 or 4 of the 4 PKA Ser2843 sites present in each RyR1 homotetramer) results in "leaky" channels (i.e., channels prone to opening at rest), which contribute to the skeletal muscle dysfunction that is associated with persistent hyperadrenergic states such as occurs in individuals with heart failure (Reiken et al., 2003).

Moreover, regulation of RyR1 by posttranslational modifications other than phosphorylation, such as by nitrosylation of free sulfhydryl groups on cysteine residues (S-nitrosylation), as well as channel oxidation, have been reported to increase RyR1 channel activity. S-nitrosylation and oxidation of RyR1 have each been shown to reduce calstabin1 binding to RyR1.

It was previously reported by Bellinger et al. (*Proc. Natl. Acad. Sci.* 2008, 105(6):2198-2002) that during extreme exercise in mice and humans, RyR1 is progressively PKA-hyperphosphorylated, S-nitrosylated and depleted of PDE4D3 and calstabin1, resulting in "leaky" channels that cause decreased exercise capacity in mice. Treatment with S107 prevented depletion of calstabin1 from the RyR1 complex, improved force generation and exercise capacity, and reduced $Ca^{2+-}$ dependent neutral protease calpain activity and plasma creatinine kinase levels.

Duchenne muscular dystrophy (DMD) is one of the leading lethal childhood genetic diseases. DMD is X-linked, affecting 1 in 3,500 male births and typically results in death by ~30 y of age from respiratory or cardiac failure. Mutations in dystrophin associated with DMD lead to a complete loss of the dystrophin protein, thereby disrupting the link between the subsarcolemma cytoskeleton and the extracellular matrix. This link is essential for protecting and stabilizing the muscle against contraction induced injury. Currently, there is no cure for DMD and most treatments in the clinic are palliative. Emerging interventions in Phase I/II clinical trials are exon skipping, myostatin inhibition, and up-regulation of utrophin. However, problems with systemic delivery, sustaining exon skipping, and up-regulation of utrophin exist. In addition, in Phase I/II clinical trials, inactivation of myostatin to increase muscle size did not show improved muscle strength or function. Sarcolemmal instability due to mutations in dystrophin has a cascade effect. One major effect is increased cytosolic $Ca^{2+}$ concentration, which leads to activation of $Ca^{2+-}$ dependent proteases (calpains). Another effect is inflammation and elevated iNOS activity, which can cause oxidation/nitrosylation of proteins, lipids, and DNA. DMD muscle pathology is progressive and far exceeds the instability of the sarcolemma. Thus the pathology is consistent with the instability of the sarcolemma increasing the susceptibility to further injury. It was recently demonstrated that excessive oxidation or nitrosylation of RyR1 can disrupt the interaction of calstabin1 with the RyR1 complex, leading to RyR1 leakiness and muscle weakness in a mouse model of muscular dystrophy (mdx) and that treatment with S107 improves indices of muscle function in this mouse model (Bellinger, A. et al. 2009, *Nature Medicine*, 15:325-330).

Age-related loss of muscle mass and force (sarcopenia) contributes to disability and increased mortality. Andersson, D. et al. (*Cell Metab.* 2011 Aug. 3; 14(2):196-207) reported that RyR1 from aged (24 months) mice is oxidized, cysteine-nitrosylated, and depleted of calstabin1, compared to RyR1 from younger (3-6 months) adults. This RyR1 channel complex remodeling resulted in "leaky" channels with increased open probability, leading to intracellular calcium leak in skeletal muscle. Treating aged mice with S107 stabilized binding of calstabin1 to RyR1, reduced intracellular calcium leak, decreased reactive oxygen species (ROS), and enhanced tetanic $Ca^{2+}$ release, muscle-specific force, and exercise capacity.

PCT International patent publications WO 2005/094457, WO 2006/101496 and WO 2007/024717 disclose 1,4-benzothiazepine derivatives and their use in treating cardiac, skeletal muscular and cognitive disorders, among others.

PCT International patent publication WO 2008/060332 relates to the use of 1,4-benzothiazepine derivatives for treating muscle fatigue in subjects suffering from pathologies such as muscular dystrophy, or in subjects suffering from muscle fatigue as a result of sustained, prolonged and/or strenuous exercise, or chronic stress.

PCT International patent publication WO 2008/021432 relates to the use of 1,4-benzothiazepine derivatives for the treatment and/or prevention of diseases, disorders and conditions affecting the nervous system.

PCT International patent publication WO 2012/019076 relates to the use of 1,4-benzothiazepine derivatives for the treatment and/or prevention of cardiac ischemia/reperfusion injury. Fauconnier et al., *Proc Natl Acad Sci USA*, 2011, 108(32): 13258-63 reported that RyR leak mediated by caspase-8 activation leads to left ventricular injury after myocardial ischemia-reperfusion, and that treatment with S107 inhibited the SR $Ca^{2+}$ leak, reduced ventricular arrhythmias, infarct size, and left ventricular remodeling at 15 days after reperfusion.

PCT International patent publication WO 2012/019071 relates to the use of 1,4-benzothiazepine derivatives for the treatment and/or prevention of sarcopenia.

PCT International patent publication WO 2012/037105 relates to the use of 1,4-benzothiazepine derivatives for the treatment and/or prevention of stress-induced neuronal disorders and diseases.

There is a need to identify new compounds effective for treating disorders and diseases associated with RyRs, including skeletal muscular and cardiac disorders and diseases. More particularly, a need remains to identify new agents that can be used to treat RyR-associated disorders by, for example, repairing the leak in RyR channels, and enhancing binding of calstabins to PKA-phosphorylated/oxidized/nitrosylated RyRs, and to mutant RyRs that otherwise have reduced affinity for, or do not bind to, calstabins.

SUMMARY OF THE INVENTION

The present invention provides novel 1,4-benzothiazepine derivatives, and their pharmaceutically acceptable salts. In some embodiments, the compounds of the present invention are ryanodine receptor (RyR) calcium channel stabilizers, sometimes referred to as "Rycals™" The present invention further provides methods of using these compounds for treating disorders and diseases associated with RyRs.

The compounds of the present invention are a selection from the 1,4-benzothiazepine derivatives described in WO 2007/024717. WO 2007/024717 describes structurally similar compounds, however, as further described herein, these compounds have been found to be highly unstable and thus their therapeutic utility as drugs is limited. The problem underlying the present application is thus to provide alternative 1,4-benzothiazepine derivatives that are not only pharmacologically active—but also have favorable properties such as high metabolic stability, and thus are suitable as drugs in treating diseases and conditions associated with the RyR, for example cardiac, skeletal muscular and central nervous system (CNS) disorders. It has unexpectedly been discovered that compounds of formula (I) are stable as well as pharmacologically active thus providing a technical solution to the problem underlying the present invention.

The compounds of the present invention are represented by the structure of Formula (I):

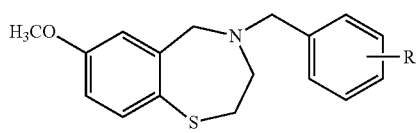

wherein
R is COOH;
and pharmaceutically acceptable salts thereof.

The compounds of Formula (I) may be present in the form of a salt with a pharmaceutically acceptable acid or base. Such salts are preferably selected from the group consisting of sodium, potassium, magnesium, hemifumarate, hydrochloride and hydrobromide salts, with each possibility representing a separate embodiment of the present invention. One currently preferred salt is the sodium salt. Another currently preferred salt is the hemifumarate salt.

In some specific embodiments, the compound is selected from the group consisting of compound 1, compound 4 and compound 6, and pharmaceutically acceptable salts thereof. The structures of these compounds are described hereinbelow.

In a preferred embodiment, the compound is represented by the structure of compound (1):

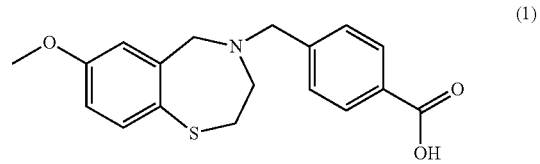 [SMILES: COc1ccc2c(c1)CN(Cc1ccc(C(=O)O)cc1)CCS2]

or pharmaceutically acceptable salts thereof.

In some embodiments, compound 1 is provided as the parent compound. In other embodiments, however, compound 1 is provided in the form of a salt with a pharmaceutically acceptable acid or base. Preferably, such salt is selected from the group consisting of sodium, potassium, magnesium, hemifumarate, hydrochloride and hydrobromide salts, with each possibility representing a separate embodiment of the present invention. One currently preferred salt is the sodium salt. Another currently preferred salt is the hemifumarate salt.

The present invention also provides methods for the synthesis of compounds of the invention, and salts thereof.

The present invention also provides pharmaceutical compositions comprising one or more of the compounds of the invention, and at least one additive or excipient, e.g., fillers, diluents, binders, disintegrants, buffers, colorants, emulsifiers, flavor-improving agents, gellants, glidants, preservatives, solubilizers, stabilizers, suspending agents, sweeteners, tonicity agents, wetting agents, emulsifiers, dispersing agents, swelling agents, retardants, lubricants, absorbents, and viscosity-increasing agents. The compositions may be presented in capsules, granules, powders, solutions, sachets, suspensions, or tablet dosage form.

The present invention further provides methods of treating or preventing various disorders, diseases and conditions associated with RyRs, such as cardiac, musculoskeletal, cognitive, CNS and neuromuscular disorders and diseases, comprising administering to a subject in need of such treatment an amount of a compound of Formula (I) or a salt thereof, effective to prevent or treat a disorder or disease associated with an RyR. The present invention also provides a method of preventing or treating a leak in RyR (including RyR1, RyR2 and RyR3) in a subject, including administering to the subject an amount of a compound of Formula (I) or a salt thereof, effective to prevent or treat a leak in RyR.

In addition, the present invention provides a method of modulating the binding of RyRs and calstabins in a subject, including administering to the subject an amount of a compound of Formula (I) or a salt thereof, effective to modulate the amount of RyR-bound calstabin.

The present invention further relates to the use of a compound of Formula (I) for the manufacture of a medicament for the treatment and/or prevention of disorders, diseases and conditions associated with RyRs, such as cardiac, musculoskeletal and cognitive/CNS disorders and diseases. In another embodiment, the present invention relates to the use of a compound of Formula (I) for the manufacture of a medicament for preventing or treating a leak in RyR. In another embodiment, the present invention relates to the use of a compound of Formula (I) for the manufacture of a medicament for modulating the amount of RyR-bound calstabins.

The methods of the invention can be practiced on an in vitro system (e.g., cultured cells or tissues) or in vivo (e.g., in a non-human animal or a human).

In some embodiments, the compounds of the invention are provided in combination with exon skipping therapy, e.g., antisense oligonucleotides (AOs) so as to enhance exon skipping in an mRNA of interest, e.g., the DMD gene, as further described herein. Other features and advantages of the present invention will become apparent from the following detailed description and figures.

BRIEF DESCRIPTION OF THE FIGURES

FIG. 4A: LV End Diastolic Volume; FIG. 4B: LV End Systolic Volume; FIG. 4C: EF. FIGS. 4A and 4B: §P<0.001 vs. sham; *P<0.05 vs. vehicle; †P<0.001 vs. vehicle. FIG. 4C: §P<0.001 vs. sham, †P<0.001 vs. vehicle.

FIGS. 5A-C: not significant. FIG. 5D: ††† P<0.001 vs. sham; *P<0.05 vs. vehicle.

FIG. 6A: not significant. FIG. 6B: §P<0.05 vs. sham; *P<0.05 vs. vehicle. FIG. 6C: †P<0.01 vs. sham; *P<0.05 vs. vehicle.

DETAILED DESCRIPTION OF THE INVENTION

Figure 1A:
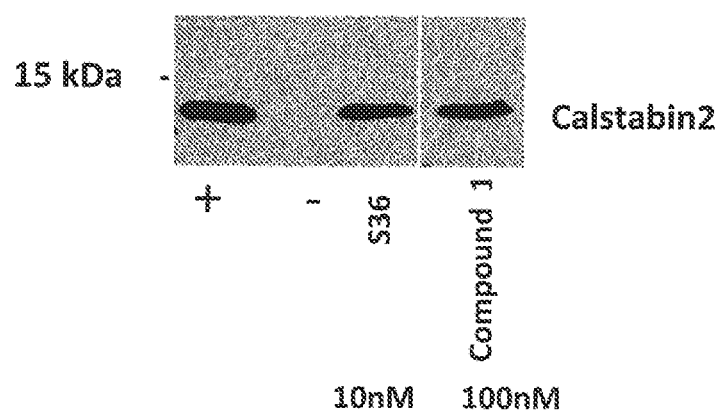
FIG. 1A Immunoblot with calstabin2 antibody showing binding of calstabin2 to PKA-phosphorylated RyR2 in the absence (−) or presence of 100 nM compound 1. (+): calstabin binding to non-PKA phosphorylated RyR2. S36 (U.S. Pat. No. 7,544,678), is used as a positive control.

It should be understood that the detailed description and the specific examples while indicating various embodiments of the invention are given by way of illustration only, since various changes and modifications within the spirit and scope of the invention will become apparent to those skilled in the art from this detailed description.

As used herein and in the appended claims, the singular forms "a," "an," and "the" include plural references unless the content clearly dictates otherwise. All publications, patent applications, patents, and other references mentioned herein are incorporated by reference in their entirety.

The term "Rycals™" refers to ryanodine receptor calcium channel stabilizers, represented by compounds of the general Formula (I) or (IA) as provided by the invention, as well as the specific compounds designated by numerical numbers as provided by the invention, and herein collectively referred to as "compound(s) of the invention".

Compounds

In some embodiments, the compounds of the present invention are represented by the structure of Formula (IA):

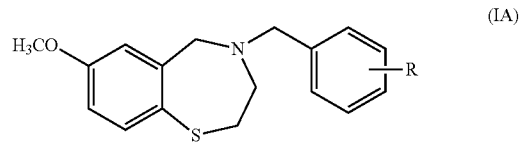

(IA)

wherein
R is COOH or a bioisostere thereof, COOR$^1$ or CN; and
R$^1$ is a $C_1$-$C_4$ alkyl;
and pharmaceutically acceptable salts thereof.

In some preferred embodiments, R in Formula (IA) is a carboxylic acid (COOH). In other preferred embodiments, R in Formula (IA) is a carboxylic acid bioisostere, for example tetrazole. Alternatively, the carboxylic acid bioisostere may be an acidic heterocycle such as 1,2,4-oxadiazol-5(4H)-one, 1,2,4-thiadiazol-5(4H)-one, 1,2,4-oxadiazole-5(4H)-thione, 1,3,4-oxadiazole-2(3H)-thione, 4-methyl-1H-1,2,4-triazole-5(4H)-thione, 5-fluoroorotic acid, and the like. Additional carboxylic acid bioisosteres are described in, e.g., Hamada, Y. et al., *Bioorg. Med. Chem. Lett.* 2006; 16:4354-4359; Herr, R. J. et al., *Bioorg. Med. Chem.* 2002; 10: 3379-3393; Olesen, P.H., *Curr. Opin. Drug Discov. Devel.* 2001; 4: 471; Patani. G. A. et al., *J. Chem. Rev.* 1996; 96:3147; Kimura, T. et al. *Bioorg. Med. Chem. Lett.* 2006; 16: 2380-2386; and Kohara, Y. et al. *Bioorg. Med. Chem. Lett.* 1995; 5(17): 1903-1908. The contents of each of the aforementioned references are incorporated by reference herein.

In one preferred embodiment, the compounds of the present invention are represented by the structure of Formula (IA) wherein R is COOH and pharmaceutically acceptable salts thereof (i.e., a compound of formula (I)).

In other preferred embodiments, R in Formula (IA) is at position 4 of the phenyl ring (i.e., position 7 of the benzothiazepine ring). Each possibility represents a separate embodiment of the present invention. The compounds of Formula (IA) or (I) may be present in the form of a salt with a pharmaceutically acceptable acid or base. Such salts are preferably selected from the group consisting of sodium, potassium, magnesium, hemifumarate, hydrochloride and hydrobromide salts, with each possibility representing a separate embodiment of the present invention. One currently preferred salt is the sodium salt. Another currently preferred salt is the hemifumarate salt.

In some specific embodiments, the compound is selected from the group consisting of compound 1, compound 2, compound 3, compound 4, compound 5, compound 6, compound 7, compound 8, compound 9, compound 10, compound 11, and compound 12, and pharmaceutically acceptable salts thereof. These compounds are represented by the following structures:

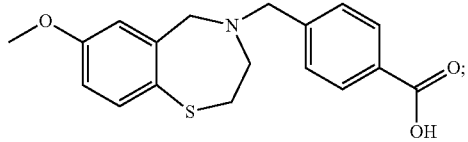
(1)

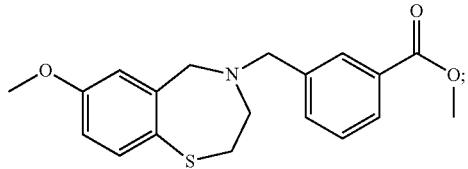
(2)

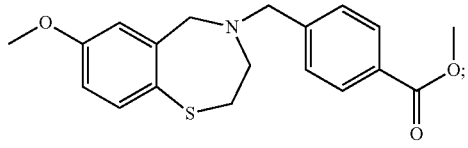
(3)

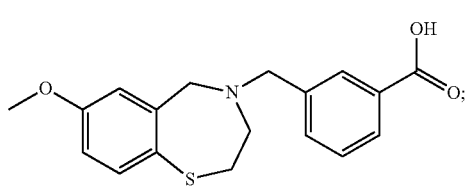
(4)

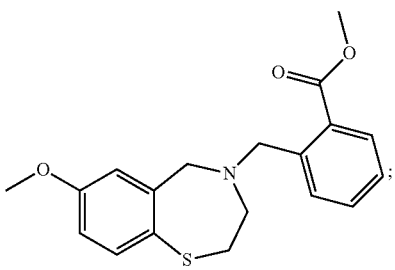
(5)

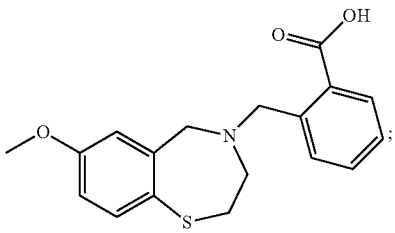
(6)

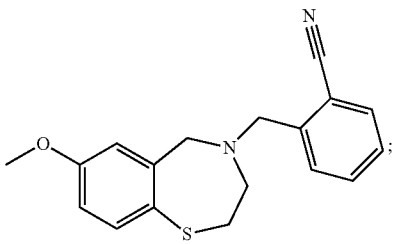
(7)

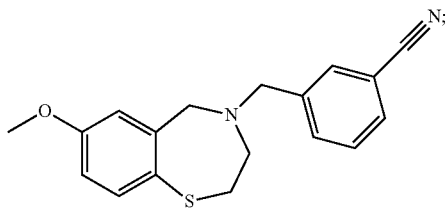
(8)

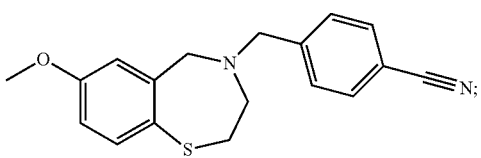
(9)

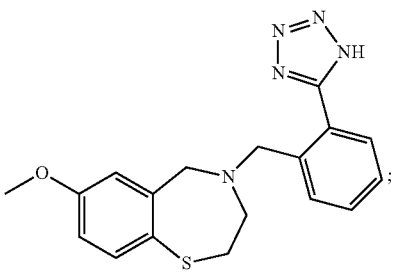
(10)

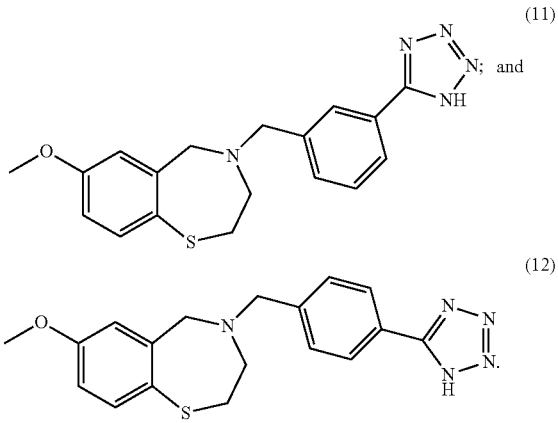

Chemical Definitions:

The term "alkyl" as used herein refers to a linear or branched, saturated hydrocarbon having from 1 to 4 carbon atoms ("$C_1$-$C_4$ alkyl"). Representative alkyl groups include, but are not limited to, methyl, ethyl, propyl, isopropyl, butyl, sec-butyl, and tert-butyl. The alkyl group may be unsubstituted or substituted by one or more groups selected from halogen, haloalkyl, hydroxy, alkoxy, haloalkoxy, cycloalkyl, aryl, heterocyclyl, heteroaryl, amido, alkylamido, dialkylamido, nitro, amino, cyano, $N_3$, oxo, alkylamino, dialkylamino, carboxyl, thio, thioalkyl and thioaryl.

Compounds of the present invention may exist in their tautomeric form. All such tautomeric forms are contemplated herein as part of the present invention.

All stereoisomers of the compounds of the present invention (for example, those which may exist due to asymmetric carbons on various substituents), including enantiomeric forms and diastereomeric forms, are contemplated within the scope of this invention. Individual stereoisomers of the compounds of the invention may, for example, be substantially free of other isomers (e.g., as a pure or substantially pure optical isomer having a specified activity), or may be admixed, for example, as racemates, or as mixtures enriched by one stereoisomer. The chiral centers of the present invention may have the S or R configuration as defined by the IUPAC 1974 Recommendations. The racemic forms can be resolved by physical methods, such as, for example, fractional crystallization, separation or crystallization of diastereomeric derivatives or separation by chiral column chromatography. The individual optical isomers can be obtained from the racemates by any suitable method, including without limitation, conventional methods, such as, for example, salt formation with an optically active acid or base, followed by crystallization.

Compounds of the present invention are, subsequent to their preparation, preferably isolated and purified to obtain a composition containing an amount by weight equal to or greater than about 90% of the compound, about 95% of the compound, and even more preferably greater than about 99% of the compound ("substantially pure" compound), which is then used or formulated as described herein. Such "substantially pure" compounds of the present invention are also contemplated herein as part of the present invention.

Therapeutic Use

The present invention provides compounds that are capable of treating conditions, disorders and diseases associated with RyRs. More particularly, the present invention provides compounds that are capable of fixing a leak in RyR channels, which may be RyR1, RyR2 and/or RyR3 channels. In one embodiment, the compounds of the invention enhance association and/or inhibit dissociation of RyR and calstabin (e.g., RyR1 and calstabin1; RyR2 and calstabin2; and RyR3 and calstabin1). "Conditions, disorders and diseases associated with RyRs" means disorders and diseases that can be treated and/or prevented by modulating RyRs and include, without limitation, cardiac disorders and diseases, muscle fatigue, musculoskeletal disorders and diseases, CNS disorders and diseases, cognitive dysfunction, neuromuscular diseases and disorders, cognitive function improvement, bone disorders and diseases, cancer cachexia, malignant hyperthermia, diabetes, sudden cardiac death, and sudden infant death syndrome.

Thus, in one embodiment, the present invention relates to a method of treating or preventing a condition selected from the group consisting of cardiac disorders and diseases, muscle fatigue, musculoskeletal disorders and diseases, CNS disorders and diseases, cognitive dysfunction, neuromuscular diseases and disorders, bone disorders and diseases, cancer cachexia, malignant hyperthermia, diabetes, sudden cardiac death, and sudden infant death syndrome, or for improving cognitive function, the method comprising the step of administering to a subject in need thereof a therapeutically effective amount of a compound of Formula (I) or (IA) as described herein, or a salt thereof, to effectuate such treatment. A currently preferred compound is a compound of Formula (I).

In another embodiment, the present invention relates to the use of an effective amount of compound of Formula (I) or (IA), as described herein, or a salt thereof, for the manufacture of a medicament for treating or preventing a condition selected from the group consisting of cardiac disorders and diseases, muscle fatigue, skeletal muscular disorders and diseases, CNS disorders and diseases, neuromuscular disorder and diseases, cognitive dysfunction, bone disorders and diseases, cancer cachexia, malignant hyperthermia, diabetes, sudden cardiac death, and sudden infant death syndrome, or for improving cognitive function. A currently preferred compound is a compound of Formula (I).

In another embodiment, the present invention relates to a compound of Formula (I) or (IA) as described herein, or a salt thereof, for use in the manufacture of a medicament for treating or preventing a condition selected from the group consisting of cardiac disorders and diseases, muscle fatigue, skeletal muscular disorders and diseases, CNS disorders and diseases, cognitive dysfunction, neuromuscular diseases and disorders, bone disorders and diseases, cancer cachexia, malignant hyperthermia, diabetes, sudden cardiac death, and sudden infant death syndrome, or for improving cognitive function. A currently preferred compound is a compound of Formula (1).

In one embodiment, the condition, disorder or disease is associated with an abnormal function of RyR1. In another embodiment, the condition, disorder or disease is associated with an abnormal function of RyR2. In another embodiment, the condition, disorder or disease is associated with an abnormal function of RyR3. Each possibility represents a separate embodiment of the present invention.

Cardiac disorders and diseases include, but are not limited to, irregular heartbeat disorders and diseases, exercise-induced irregular heartbeat disorders and diseases, heart failure, congestive heart failure, chronic heart failure, acute heart failure, systolic heart failure, diastolic heart failure, acute decompensated heart failure, cardiac ischemia/reperfusion (I/R) injury (including I/R injury following coronary angioplasty or following thrombolysis during myocardial infarction (MI)), chronic obstructive pulmonary disease, and high blood pressure. Irregular heartbeat disorders and diseases include, but are not limited to atrial and ventricular arrhythmia, atrial and ventricular fibrillation, atrial and ventricular tachyarrhythmia, atrial and ventricular tachycardia, catecholaminergic polymorphic ventricular tachycardia (CPVT), and exercise-induced variants thereof.

The compounds of the invention are also useful in treating muscle fatigue, which may be due to prolonged exercise or high-intensity exercise, or may be caused by musculoskeletal diseases. Examples of muscular disorders and diseases include, but are not limited to, skeletal muscle fatigue, central core diseases, exercise-induced skeletal muscle fatigue, bladder disorders, incontinence, age-associated muscle fatigue, sarcopenia, congenital myopathies, skeletal muscle myopathies and/or atrophies, cancer cachexia, myopathy with cores and rods, mitochondrial myopathies [e.g., Kearns-Sayre syndrome, MELAS (mitochondrial myopathy, encephalopathy, lactic acidosis, and stroke) syndrome, and MERRF (myoclonus epilepsy with ragged-red fibers) syndrome], endocrine myopathies, muscular glycogen storage diseases [e.g., Pompe's disease, Andersen's disease, and Cori's diseases], myoglobinurias [e.g., McArdle's disease, Tarui disease, and DiMauro disease], dermatomyositis, myositis ossificans, familial periodic paralysis, polymyositis, inclusion body myositis, neuromyotonia, stiff-man syndrome, malignant hyperthermia, common muscle cramps, tetany, myasthenia gravis, spinal muscular atrophy (SMA), Spinal and bulbar muscular atrophy (SBMA, also known as spinobulbar muscular atrophy, bulbo-spinal atrophy, X-linked bulbospinal neuropathy (XBSN), X-linked spinal muscular atrophy type 1 (SMAX1), and Kennedy's disease (KD)), and muscular dystrophy. Preferred skeletal muscular disorders include, but are not limited to exercise-induced skeletal muscle fatigue, a congenital myopathy, muscular dystrophy, age-related muscle fatigue, sarcopenia, central core disease, cancer cachexia, bladder disorders, and incontinence.

Examples of muscular dystrophy include, but are not limited to, Duchenne Muscular Dystrophy (DMD), Becker's Muscular Dystrophy (BMD), Limb Girdle Muscular Dystrophy (LGMD), Congenital Muscular Dystrophy (CMD), distal muscular dystrophy, facioscapulohumeral dystrophy, myotonic muscular dystrophy, Emery-Dreifuss muscular dystrophy, and oculopharyngeal muscular dystrophy, with DMD being currently preferred.

Congenital muscular dystrophy as used herein refers to muscular dystrophy that is present at birth. CMD is classified based on genetic mutations: 1) genes encoding for structural proteins of the basal membrane or extracellular matrix of the skeletal muscle fibres; 2) genes encoding for putative or demonstrated glycosyltransferases, that in turn affect the glycosylation of dystroglycan, an external membrane protein of the basal membrane; and 3) other. Examples of CMD include, but are not limited to Laminin-α2-deficient CMD (MDC1A), Ullrich CMG (UCMDs 1, 2 and 3), Walker-Warburg syndrome (WWS), Muscle-eye-brain disease (MEB), Fukuyama CMD (FCMD), CMD plus secondary laminin deficiency 1 (MDC1B), CMD plus secondary laminin deficiency 2 (MDC1C), CMD with mental retardation and pachygyria (MDC1D), and Rigid spine with muscular dystrophy Type 1 (RSMD1).

Cognitive dysfunction may be associated with or includes, but is not limited to memory loss, age-dependent memory loss, post-traumatic stress disorder (PTSD), attention deficit hyperactivity disorder (ADHD), autism spectrum disorder (ASD), generalized anxiety disorder (GAD), obsessive compulsive disorder (OCD), Schizophrenia, Bipolar disorder, or major depression CNS disorders and diseases include, but are not limited to Alzheimer's Disease (AD), neuropathy, seizures, Parkinson's Disease (PD), and Huntington's Disease (HD).

Neuromuscular disorders and diseases include, but are not limited to Spinocerebellar ataxia (SCA), and Amyotrophic lateral sclerosis (ALS, Lou Gehrig's disease).

In some embodiments, the compounds of the present invention improve cognitive function, which may be selected from short term memory, long term memory, attention, learning, and any combination thereof.

In some embodiments, the compounds of the present invention are useful in the treatment of cancer cachexia, i.e., muscle weakness which is associated with cancer in general, and preferably muscle weakness in metastatic cancer, such as bone metastases. Muscle weakness and muscle atrophy (cachexia) are common paraneoplastic symptoms in cancer patients. These conditions cause significant fatigue and dramatically reduce patients' quality of life. The present invention provides a method for treating and preventing muscle weakness in a cancer patient, based, in part, on the discovery that, in certain types of cancers, e.g., prostate and breast cancer with bone metastases, RyR1 is oxidized which induces it to become "leaky". It has further been found that prevention of the leak by administration of Rycal compounds improves muscle function. Exemplary cancers include, but are not limited to, breast cancer, prostate cancer, bone cancer, pancreatic cancer, lung cancer, colon cancer, and gastrointestinal cancer.

Exon Skipping Therapy:

In some embodiments, the compounds of the present invention modulate (e.g., enhance) mRNA splicing by enhancing antisense-mediated exon skipping. This modulation of splicing is accomplished in the presence of antisense oligonucleotides (AOs) that are specific for splicing sequences of interest. In some embodiments of the invention, the compound of formula (I) or (IA) and the AO can act synergistically wherein the compound of formula (I) or (IA) enhances AO mediated exon skipping. Thus, in some embodiments, the present invention relates to a pharmaceutical composition for use in the treatment or prevention of any of the conditions described herein that are associated with Leaky RyR, further comprising the use of an antisense AO which is specific for a splicing sequence in an mRNA sequence, for enhancing exon skipping in the mRNA of interest.

One particular embodiment for exon skipping enhancement by the compounds of the present invention pertains to Duchenne Muscular Dystrophy (DMD). DMD is a lethal X-linked recessive disease characterized by progressive muscle weakness over a patient's lifetime. DMD is primarily caused by out of frame multi-exon deletions in the DMD gene that ablate dystrophin protein production. Loss of dystrophin expression alone does not explain DMD pathophysiology. Disruption of the dystrophin-glycoprotein complex (DGC) also results in oxidative stress, mitochondrial $Ca^{2+}$ overload and apoptosis, increased influx of $Ca^{2+}$ into the muscle, and pathologic $Ca^{2+}$ signaling. There are no curative therapies for DMD, and the only demonstrated pharmacological treatment is corticosteroids, which may prolong ambulation, but have substantial side effects. Antisense oligonucleotide-mediated exon skipping is a promising therapeutic approach aimed at restoring the DMD reading frame and allowing expression of an intact dystrophin glycoprotein complex. To date, low levels of dystrophin protein have been produced in humans by this method. Kendall et al. (*Sci Transl Med*, 2012, 4(164), p. 164ra160) reported that certain small molecules such as Dantrolene and other RyR modulators, potentiate antisense oligomer-guided exon skipping to increase exon skipping to restore the mRNA reading frame, the sarcolemmal dystrophin protein, and the dystrophin glycoprotein complex in skeletal muscle of mdx mice, a mouse model of DMD.

Thus, in one embodiment, the present invention relates to a method for treating DMD, by administering to a subject in need thereof a compound of formula (I) or (IA) according to the present invention, in combination with an antisense oligonucleotide (AO) which is specific for a splicing sequence of one or more exons of the DMD gene, for example exon 23, 45, 44, 50, 51, 52 and/or 53 of the DMD gene. Preferred AOs include, but are not limited to, AOs targeting DMD exon 23, 50 and/or 51 of the DMD gene, such as 2'-O-methyl (2'OMe) phosphorothioate or phosphorodiamidate morpholino (PMO) AOs. Examples of such AOs include, but not limited to, Pro051/GSK2402968, AVI4658/Eteplirsen, and PMO E23 morpholino (5'-GGCCAAACCTCGGCTTACCT-GAAAT-3', SEQ ID NO:1).

The term an "effective amount," "sufficient amount" or "therapeutically effective amount" of an agent as used herein interchangeably, is that amount sufficient to effectuate beneficial or desired results, including clinical results and, as such, an "effective amount" or its variants depends upon the context in which it is being applied. The response is in some embodiments preventative, in others therapeutic, and in others a combination thereof. The term "effective amount" also includes the amount of a compound of the invention, which is "therapeutically effective" and which avoids or substantially attenuates undesirable side effects.

As used herein and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e., not worsening) state of disease, preventing spread of disease, delay or slowing of disease progression, amelioration or palliation of the disease state and remission (whether partial or total), whether detectable or undetectable. "Treatment" can also mean prolonging survival as compared to expected survival if not receiving treatment.

Pharmaceutical Compositions

The compounds of the invention are formulated into pharmaceutical compositions for administration to human subjects in a biologically compatible form suitable for administration in vivo. According to another aspect, the present invention provides a pharmaceutical composition comprising compounds of the invention in admixture with a pharmaceutically acceptable diluent and/or carrier. The pharmaceutically-acceptable carrier is preferably "acceptable" in the sense of being compatible with the other ingredients of the composition and not deleterious to the recipient thereof.

The compound may be administered alone, but is preferably administered with one or more pharmaceutically acceptable carriers. The pharmaceutically-acceptable carrier employed herein may be selected from various organic or inorganic materials that are used as materials for pharmaceutical formulations and which are incorporated as any one or more of fillers, diluents, binders, disintegrants, buffers, colorants, emulsifiers, flavor-improving agents, gellants, glidants, preservatives, solubilizers, stabilizers, suspending agents, sweeteners, tonicity agents, wetting agents, emulsifiers, dispersing agents, swelling agents, retardants, lubricants, absorbents, and viscosity-increasing agents.

The compounds of the present invention are administered to a human or animal subject by known procedures including, without limitation, oral, sublingual, buccal, parenteral (intravenous, intramuscular or subcutaneous), transdermal, per- or trans-cutaneous, intranasal, intra-vaginal, rectal, ocular, and respiratory (via inhalation administration). The compounds of the invention may also be administered to the subject by way of delivery to the subject's muscles including, but not limited to, the subject's cardiac or skeletal muscles. In one embodiment, the compound is administered to the subject by way of targeted delivery to cardiac muscle cells via a catheter inserted into the subject's heart. In other embodiments, the compounds may be administered directly into the CNS, for example by intralumbar injection or intreventricular infusion of the compounds directly into the cerebrospinal-fluid (CSF), or by intraventricular, intrathecal or interstitial administration. Oral administration is currently preferred.

The pharmaceutical compositions according to the invention for solid oral administration include especially tablets or dragées, sublingual tablets, sachets, capsules including gelatin capsules, powders, and granules, and those for liquid oral, nasal, buccal or ocular administration include especially emulsions, solutions, suspensions, drops, syrups and aerosols. The compounds may also be administered as a suspension or solution via drinking water or with food. Examples of acceptable pharmaceutical carriers include, but are not limited to, cellulose derivatives including carboxymethyl cellulose, methyl cellulose, hydroxypropyl cellulose, hydroxypropylmethylcellulose, ethyl cellulose and microcrystalline cellulose; sugars such as mannitol, sucrose, or lactose; glycerin, gum arabic, magnesium stearate, sodium stearyl fumarate, saline, sodium alginate, starch, talc and water, among others.

The pharmaceutical compositions according to the invention for parenteral injections include especially sterile solutions, which may be aqueous or non-aqueous, dispersions, suspensions or emulsions and also sterile powders for the reconstitution of injectable solutions or dispersions. The compounds of the invention may be combined with a sterile aqueous solution that is isotonic with the blood of the subject. Such a formulation is prepared by dissolving a solid active ingredient in water containing physiologically-compatible substances, such as sodium chloride, glycine and the like, and having a buffered pH compatible with physiological conditions, so as to produce an aqueous solution, then rendering said solution sterile. The formulation is presented in unit or multi-dose containers, such as sealed ampoules or vials. The formulation is delivered by any mode of injection, including, without limitation, epifascial, intracapsular, intracranial, intracutaneous, intrathecal, intramuscular, intraorbital, intraperitoneal, intraspinal, intrasternal, intravascular, intravenous, parenchymatous, subcutaneous, or sublingual or by way of catheter into the subject's heart.

The pharmaceutical compositions for rectal or vaginal administration are preferably suppositories, and those for per- or trans-cutaneous administration include especially powders, aerosols, creams, ointments, gels and patches.

For transdermal administration, the compounds of the invention are combined with skin penetration enhancers, such as propylene glycol, polyethylene glycol, isopropanol, ethanol, oleic acid, N-methylpyrrolidone and the like, which increase the permeability of the skin to the compounds of the invention and permit the compounds to penetrate through the skin and into the bloodstream. The compound/enhancer compositions also may be further combined with a polymeric substance, such as ethylcellulose, hydroxypropyl cellulose, ethylene/vinylacetate, polyvinyl pyrrolidone, and the like, to provide the composition in gel form, which is dissolved in a solvent, evaporated to the desired viscosity and then applied to backing material to provide a patch.

The pharmaceutical formulations of the present invention are prepared by methods well-known in the pharmaceutical arts, including but not limited to wet and dry granulation methods, or by direct compression. The choice of carrier is determined by the solubility and chemical nature of the compounds, chosen route of administration and standard pharmaceutical practice.

The pharmaceutical compositions mentioned above illustrate the invention but do not limit it in any way.

In accordance with the methods of the present invention, any of these compounds may be administered to the subject (or are contacted with cells of the subject) in an amount effective to limit or prevent a decrease in the level of RyR-bound calstabin in the subject, particularly in cells of the subject. This amount is readily determined by the skilled artisan, based upon known procedures, including analysis of titration curves established in vivo and methods and assays disclosed herein. A suitable amount of the compounds of the invention effective to limit or prevent a decrease in the level of RyR-bound calstabin in the subject ranges from about 0.01 mg/kg/day to about 100 mg/kg/day (e.g., 1, 2, 5, 10, 20, 25, 50 or 100 mg/kg/day), and/or is an amount sufficient to achieve plasma levels ranging from about 300 ng/ml to about 5,000 ng/ml. Alternatively, the amount of compounds from the invention ranges from about 1 mg/kg/day to about 50 mg/kg/day. Alternatively, the amount of compounds from the invention ranges from about 10 mg/kg/day to about 20 mg/kg/day. Also included are amounts of from about 0.01 mg/kg/day or 0.05 mg/kg/day to about 5 mg/kg/day or about 10 mg/kg/day which can be administered.

Methods of Synthesis

The present invention provides, in a further aspect, processes for the preparation of a compound of the invention, and salts thereof. More particularly, the present invention provides processes for the preparation of compounds of Formula (I) or (IA), e.g., compound 1, compound 2, compound 3, compound 4, compound 5, compound 6, compound 7, compound 8, compound 9, compound 10, compound 11, and compound 12, or salts thereof. The various synthetic routes to the compounds are described in the examples. The general route of synthesis (ROS) is set forth in Scheme 1 below:

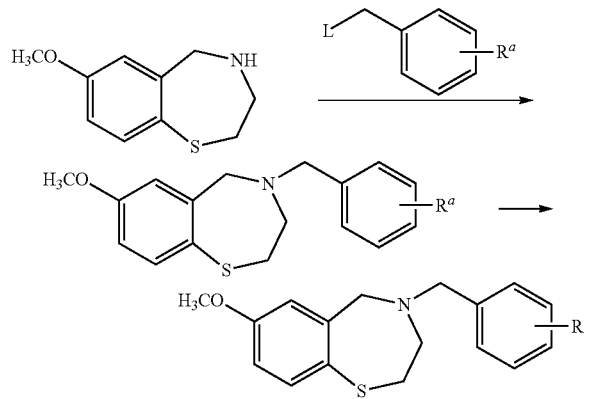

Scheme 1

In Scheme 1, $R^a$COOR$^1$ or CN; $R^1$ is a $C_1$-$C_4$ alkyl, and L is a leaving group, which is, by way of example, a halogen, a sulfonate (OSO$_2$R' wherein R' is alkyl or aryl, e.g., OMs (mesylate), OTs (tosylate)), and the like. The amine starting material is reacted with the alkylating agent (benzyl derivative shown above), preferably in the presence of a base, to yield the desired product or a precursor thereof (R=$R^a$). If desired, such precursor may further be reacted to convert the group $R^a$ to the group R as exemplified in the experimental section hereinbelow, or by any other method known to a person of skill in the art. For example, an ester precursor ($R^a$=COOR$^1$ wherein R$^1$ is a $C_1$-$C_4$ alkyl), can be converted into the corresponding carboxylic acid (R=COOH) by hydrolysis under acidic or basic conditions in accordance with known methods. Alternatively, a nitrile precursor ($R^a$=CN) can be converted into a tetrazole (a carboxylic acid isostere) by reaction with sodium azide under suitable conditions, or to a carboxylic acid (R=COOH) by hydrolysis.

The amine starting material may be prepared in accordance with the methods described in WO 2009/111463 or WO 2007/024717, or by any other method known to a person of skill in the art. The contents of all of the aforementioned references are incorporated by reference herein. The nature of the base is not particularly limiting. Preferred bases include, but are not limited to, hydrides (e.g., sodium or potassium hydride) and N,N-diisopropylethylamine. Other suitable bases include, but are not limited to an organic base such as a tertiary amine, selected from the group consisting of acyclic amines (e.g., trimethylamine, triethylamine, dimethylphenylamine diisopropylethylamine and tributylamine), cyclic amines (e.g., N-methylmorpholine) and aromatic amines (dimethylaniline, dimethylaminopyridine and pyridine).

The reaction may be conducted in the presence or absence of a solvent. The nature of the solvent, when used, is not particularly limiting, with examples including solvents such an ester (e.g., ethyl acetate), an ether (e.g., THF), a chlorinated solvent (e.g., dichloromethane or chloroform), dimethylformamide (DMF), and other solvents such as acetonitrile or toluene or mixtures of these solvents with each other or with water.

Salts of compounds of formula (I) wherein R=COOH may be prepared by reacting the parent molecule with a suitable base, e.g., NaOH or KOH to yield the corresponding alkali metal salts, e.g., the sodium or potassium salts. Alternatively, esters (R=COOR$^1$) may be directly converted to salts by reactions with suitable bases.

Salts of compounds of formula (I) may also be prepared by reacting the parent molecule with a suitable acid, e.g., HCl, fumaric acid, or para-toluenesulfonic acid to yield the corresponding salts, e.g., hydrochloride, tosylate or hemi-fumarate.

EXAMPLES

The following examples are provided as illustrations of the some preferred embodiments according to the invention.

Example 1

Synthesis

Instruments:
NMR: Bruker AVANCE III 400 or Varian Mercury 300
LC/MS: Waters Delta 600 equipped with Autosampler 717Plus, Photo Diode Array Detector 2996, and Mass Detector 3100, or Shimadzu 210

General Procedure for the alkylation of 7-methoxy-2,3,4,5-tetrahydrobenzo[f][1,4]thiazepine ("Amine")

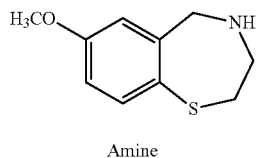 [SMILES: COc1ccc2c(c1)CNCCS2]

Amine

Amine (structure shown above) (1 mmol) was dissolved in 3 ml dichloromethane. To the solution was added alkylation reagent (1 mmol), followed by N,N-diisopropylethylamine (0.34 ml, 2 mmol). The mixture was stirred at room temperature overnight. The solution was loaded onto column directly and eluted with hexane/EtOAc (2:1, v/v).

Compound 2

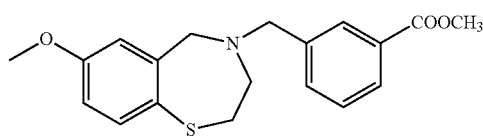

Methyl 3-((7-methoxy-2,3-dihydrobenzo[f][1,4]thiazepin-4(5H)-yl)methyl)benzoate: $^1$HNMR (300 MHz, CDCl$_3$): 7.96 (m, 2H), 7.46 (m, 3H), 6.70 (dd, J=8.4 Hz, 3.0 Hz, 1H), 6.50 (d, J=2.7 Hz, 1H), 4.09 (s, 2H), 3.90 (s, 3H), 3.72 (s, 3H), 3.57 (s, 2H), 3.35 (m, 2H), 2.72 (m, 2H). MS: 344 (M+1)

Compound 3

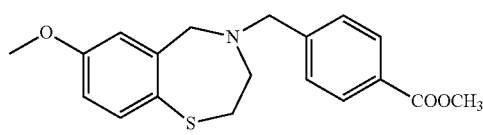

Methyl 4-((7-methoxy-2,3-dihydrobenzo[f][1,4]thiazepin-4(5H)-yl)methyl)benzoate: $^1$HNMR (300 MHz, CDCl$_3$): 7.99 (d, J=8.4 Hz, 2H), 7.46 (d, J=8.4 Hz, 1H), 7.37 (d, J=8.7 Hz, 2H), 6.70 (dd, J=8.4 Hz, 3.0 Hz, 1H), 6.50 (d, J=2.7 Hz, 1H), 4.09 (s, 2H), 3.90 (s, 3H), 3.72 (s, 3H), 3.57 (s, 2H), 3.35 (m, 2H), 2.72 (m, 2H). MS: 344 (M+1)

Compound 5

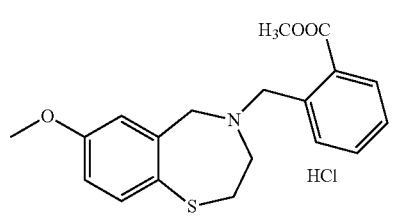

Methyl 2-((7-methoxy-2,3-dihydrobenzo[f][1,4]thiazepin-4(5H)-yl)methyl)benzoate: The compound was converted to hydrochloride salt with 2M HCl in ether. $^1$HNMR (300 MHz, DMSO-d$_6$): 10.33 (br, 1H), 8.08 (d, J=7.5 Hz, 1H), 7.80-7.65 (m, 3H), 7.51 (d, J=8.1 Hz, 1H), 7.14 (s, 1H), 6.99 (dd, J=8.4, 2.1 Hz, 1H), 4.90-4.40 (m, br, 4H), 3.88 (s, 3H), 3.78 (s, 3H), 3.40 (m, 2H), 3.26 (m, 1H), 3.11 (m, 1H). MS: 344 (M+1)

Compound 7

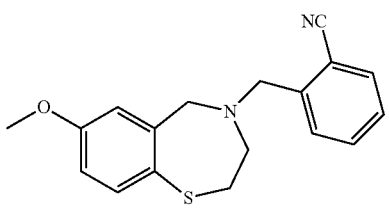

2-((7-Methoxy-2,3-dihydrobenzo[f][1,4]thiazepin-4(5H)-yl)methyl)benzonitrile: $^1$HNMR (300 MHz, CDCl3): 7.67-7.26 (m, 5H), 6.73 (d, J=2.7 Hz, 1H), 6.74 (dd, J=2.7, 8.4 Hz, 1H), 4.14 (s, 2H), 3.78 (s, 3H), 3.70 (s, 2H), 3.36 (m, 2H), 2.76 (m, 2H). MS: 311 (M+1)

Compound 8

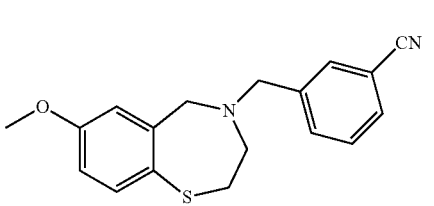

3-((7-Methoxy-2,3-dihydrobenzo[f][1,4]thiazepin-4(5H)-yl)methyl)benzonitrile: $^1$HNMR (300 MHz, CDCl3): 7.64-7.42 (m, 5H), 6.74 (dd, J=2.7, 8.4 Hz, 1H), 6.48 (d, J=2.7 Hz, 1H), 4.08 (s, 2H), 3.75 (s, 3H), 3.57 (s, 2H), 3.36 (m, 2H), 2.76 (m, 2H). MS: 311 (M+1)

Compound 9

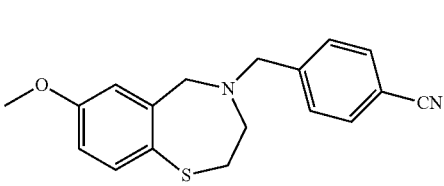

4-((7-Methoxy-2,3-dihydrobenzo[f][1,4]thiazepin-4(5H)-yl)methyl)benzonitrile: $^1$HNMR (300 MHz, CDCl3): 7.64 (d, J=7.2 Hz, 2H), 7.42 (m, 3H), 6.74 (dd, J=2.7, 8.4 Hz, 1H), 6.48 (d, J=2.7 Hz, 1H), 4.08 (s, 2H), 3.75 (s, 3H), 3.58 (s, 2H), 3.36 (m, 2H), 2.76 (m, 2H). MS: 311 (M+1)

Hydrolysis of Ester (General Procedure)

Methyl ester (3 mmol) was dissolved in 30 ml of THF/methanol/1 M NaOH (1:1:1, v/v). The mixture was stirred for 8 hours and TLC showed complete disappearance of the ester. 1 ml Conc. HCl was added to adjust to acidic pH. The organic solvent was removed and the formed solid was collected by filtration. The solid was dried in the air.

Compound 4

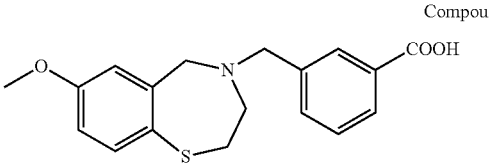

3-((7-Methoxy-2,3-dihydrobenzo[f][1,4]thiazepin-4(5H)-yl)methyl)benzoic acid: This was obtained by extraction with EtOAc as solvent. ¹HNMR (300 MHz, CDCl₃): 8.10 (s, 1H), 8.04 (d, J=8.4 Hz, 1H), 7.80 (br, 1H), 7.46 (m, 2H), 6.80 (m, 2H), 4.40 (s, 2H), 3.90 (s, 2H), 3.76 (s, 3H), 3.42 (s, 2H), 2.86 (s, 2H). MS: 330 (M+1), 328 (M−1).

Compound 1

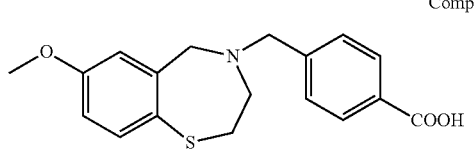

4-((7-Methoxy-2,3-dihydrobenzo[f][1,4]thiazepin-4(5H)-yl)methyl)benzoic acid: This was obtained by extraction with EtOAc as solvent. ¹HNMR (300 MHz, CDCl₃): 8.02 (d, J=8.4 Hz, 2H), 7.46 (d, J=8.4 Hz, 1H), 7.42 (d, J=8.7 Hz, 2H), 6.70 (dd, J=8.4 Hz, 3.0 Hz, 1H), 6.50 (d, J=3.0 Hz, 1H), 4.11 (s, 2H), 3.72 (s, 3H), 3.62 (s, 2H), 3.35 (m, 2H), 2.76 (m, 2H). MS: 330 (M+1), 328 (M−1).

Compound 1, Sodium Salt:

The sodium salt of compound 1 was prepared from the parent molecule using 1 equivalent of NaOH in EtOH (m.p. of the salt: >290° C.).

¹HNMR (DMSO-D6, 600 MHz), δ (ppm): 7.77 (2H, m), 7.41 (1H, d), 7.13 (2H, m), 6.75 (1H, dd), 6.63 (1H, d), 4.00 (2H, s), 3.70 (3H, s), 3.49 (2H, s), 3.18 (2H, m), 2.70 (2H, m).

Compound 1, Hemifumarate Salt:

1.6 g of compound 1 (neutral form) and 265 mg of fumaric acid were introduced in a round bottom flask. After addition of 18 mL of acetone and 2 mL of water, the reaction mixture was refluxed. A partial solubilisation was observed (but no complete clarification) followed by precipitation. The reaction mixture was then refluxed overnight. After cooling the residual solid was isolated by filtration, washed with 3 mL of acetone and dried under vacuum (40° C./10 mbars) for 4 hours.

¹HNMR (DMSO-D6, 600 MHz), δ (ppm): 12.97 (2H, bs), 7.90 (2H, m), 7.43 (1H, d), 7.40 (2H, m), 6.77 (1H, dd), 6.64 (1H, d), 6.62 (1H, s), 4.03 (2H, s), 3.70 (3H, s), 3.58 (2H, s), 3.20 (2H, m), 2.72 (2H, m).

Compound 6

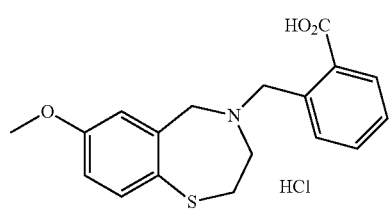

2-((7-Methoxy-2,3-dihydrobenzo[f][1,4]thiazepin-4(5H)-yl)methyl)benzoic acid: The compound was converted to hydrochloride salt with 2M HCl in ether. ¹HNMR (300 MHz, DMSO-d₆): 10.10 (br, 1H), 8.08 (d, J=7.5 Hz, 1H), 7.66-7.51 (m, 4H), 7.17 (d, J=2.1 Hz, 1H), 6.99 (dd, J=8.4, 2.1 Hz, 1H), 4.80-4.40 (m, br, 4H), 3.78 (s, 3H), 3.46 (m, 2H), 3.13 (m, 2H). MS: 330 (M+1), 328 (M−1).

Synthesis of Tetrazole (General Procedure)

Nitrile precursor (3.22 mmol), sodium azide (830 mg, 12.9 mmol) and triethylamine hydrochloride (1.72 g, 12.9 mmol) were stirred in 40 ml anhydrous DMF at 100° C. for 5 days. The DMF was removed under high vacuum and the residue was mixed with water. The water solution was extracted with dichloromethane (3×100 ml), The pure compound was purified by column chromatography (EtOAc/methanol).

Compound 10

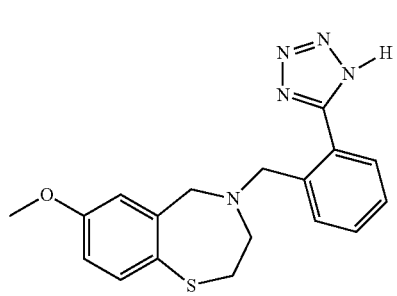

4-(2-(1H-Tetrazol-5-yl)benzyl)-7-methoxy-2,3,4,5-tetrahydrobenzo[f][1,4]thiazepine:

¹HNMR (300 MHz, CDCl3 and a drop of CD3OD): 8.30 (d, J=8.7 Hz, 1H), 7.53 (m, 2H). 7.14 (t, J=7.8 Hz, 1H), 7.20 (d, J=7.5 Hz, 1H), 6.84 (dd, J=2.7, 8.4 Hz, 1H), 6.69 (d, J=2.7 Hz, 1H), 4.46 (s, 2H), 3.80 (s, 2H), 3.75 (s, 2H), 3.43 (m, 2H), 2.96 (m, 2H). MS: 354 (M+1), 352 (M−1)

Compound 11

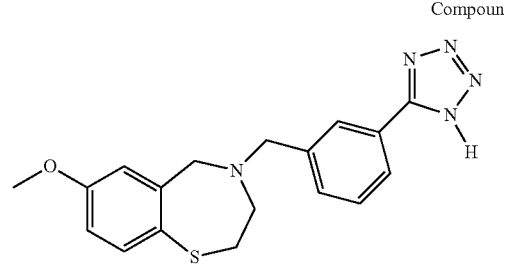

4-(3-(1H-Tetrazol-5-yl)benzyl)-7-methoxy-2,3,4,5-tetrahydrobenzo[f][1,4]thiazepine:

¹HNMR (300 MHz, CDCl3): 8.16 (s, 1H), 7.90 (d, J=7.5 Hz, 1H), 7.40 (d, J=8.4 Hz, 1H), 7.20 (m, 2H), 6.74 (dd, J=2.7, 8.4 Hz, 1H), 6.58 (d, J=2.7 Hz, 1H), 4.18 (s, 2H), 3.75 (s, 5H), 3.36 (m, 2H), 2.76 (m, 2H).). MS: 354 (M+1), 352 (M−1)

Compound 12

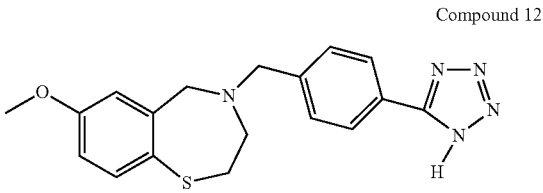 [SMILES: COc1ccc2c(c1)CN(Cc1ccc(-c3nnn[nH]3)cc1)CCS2]

4-(4-(1H-Tetrazol-5-yl)benzyl)-7-methoxy-2,3,4,5-tetrahydrobenzo[f][1,4]thiazepine:

¹HNMR (300 MHz, CDCl3 and a drop of CD3OD): 7.99 (d, J=7.2 Hz, 2H), 7.42 (m, 3H), 6.74 (dd, J=2.7, 8.4 Hz, 1H), 6.53 (d, J=2.7 Hz, 1H), 4.10 (s, 2H), 3.71 (s, 3H), 3.58 (s, 2H), 3.36 (m, 2H), 2.76 (m, 2H).). MS: 354 (M+1), 352 (M−1)

Synthesis of 7-methoxy-2,3,4,5-tetrahydrobenzo[f][1,4]thiazepine ("Amine")

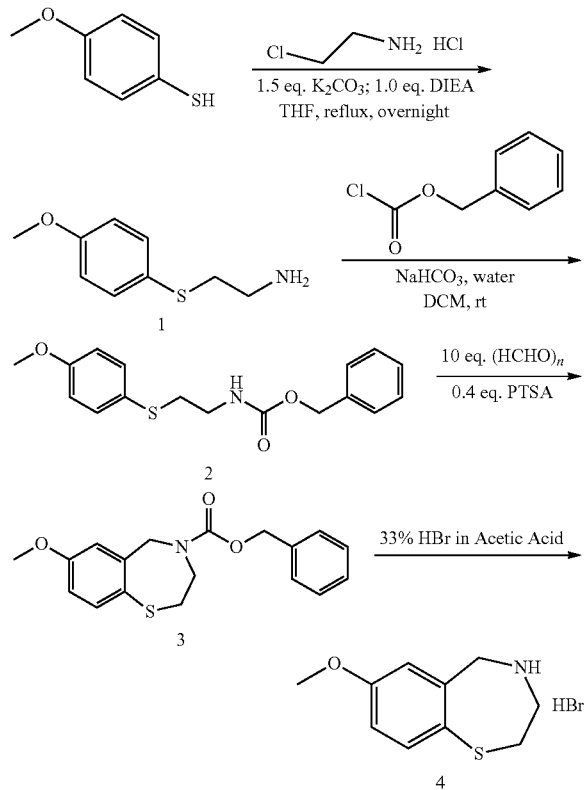

2-(4-Methoxyphenylthio)ethanamine (1)

4-Methoxythiophenol (50 g, 0.357 mol), 2-chloroethylamine monohydrochloride (39.8 g, 0.343 mol.), $K_2CO_3$ (78.8 g, 0.57 mol) and diisopropyl ethylamine (32 mL, 0.178 mol) were mixed in 200 mL of THF. The mixture was degassed for 5 min. under reduced pressure and refluxed under argon overnight. The solvent was removed and water (300 mL) was added to the flask. The mixture was extracted with dichloromethane (3×200 mL). The organics were collected, dichloromethane was removed and 50 mL conc. HCl was added, followed by 200 mL of water. The solution was extracted with 1:1 EtOAc/hexane (3×200 mL). The aqueous layer was adjusted to pH 10 with 2 M NaOH, and was extracted with dichloromethane (3×200 mL). The combined organic solution was dried over anhydrous sodium sulfate. Removal of solvent provided 61 g of the target compound as a colorless liquid, with a yield of 97%.

$^1$H-NMR (300 MHz, $CDCl_3$): 7.35 (d, J=8.7 Hz, 2H), 6.81 (d, J=8.7 Hz, 2H), 3.77 (s, 3H), 2.88-2.80 (m, 4H), 1.44 (s, 2H).

Benzyl 2-(4-methoxyphenylthio)ethylcarbamate (2)

First Method

To a the flask containing compound 1 (8.0 g, 43.7 mmol), sodium bicarbonate (12.1 g, 144 mmol), water (100 mL) and dichloromethane (200 mL) was added benzyl chloroformate (8.2 g, 48.1 mmol, diluted in 100 mL of dichloromethane) dropwise at 0° C. After the addition, the mixture was stirred at r.t. for 5 hr. The organic layer was collected and aqueous solution was extracted with 100 mL of dichloromethane. The combined organic solution was dried over sodium sulfate. The solvent was removed and the resulting solid was triturated with 200 mL of THF/hexane (1:10). The solid was collected and dried leaving the target product (12.9 g) in the yield of 93%.

Alternative Method

To the solution of compound 1 (10 g, 54.6 mmol) and triethylamine (15 mL, 106 mmol) in 200 mL of dichloromethane was added benzyl chloroformate (7.24 mL, 51.5 mmol, diluted in 100 mL of dichloromethane) dropwise at 0° C. After the addition, the solution was stirred at r.t. for one hour. The solid was removed by filtration. The solution was extracted with 100 mL of 0.1 M HCl and 100 mL of sat. sodium carbonate, and dried over anhydrous sodium sulfate. Removal of solvent provided a white solid that was stirred in 200 mL of THF/hexane (1:20) for three hours. The solid was collected by filtration to give 14.2 g of the target compound in 87% yield.

$^1$H-NMR (300 MHz, $CDCl_3$): 7.35 (m, 7H), 6.83 (d, J=8.7 Hz, 2H), 5.07 (m, 3H), 3.77 (s, 3H), 3.10 (q, J=6.3 Hz, 2H), 2.92 (t, J=6.3 Hz, 2H).

Benzyl 7-methoxy-2,3-dihydrobenzo[f][1,4]thiazepine-4(5H)-carboxylate (3)

A mixture of compound 2 (7.3 g, 23 mmol), paraformaldehyde (6.9 g 0.23 mol) and p-toluenesulfonic acid (1.45 g, 7.6 mmol) in 250 mL of toluene was stirred at 70° C. overnight. After cooling to r.t., the solid was filtered off. The solution was extracted with sat. sodium carbonate (100 mL), and the organic layer was dried over anhydrous sodium sulfate. The target product (7.4 g) was obtained as a liquid after removal of the solvent in 97% yield.

$^1$H-NMR (300 MHz, $CDCl_3$): 7.44 (d, J=8.1 Hz, 0.77H), 7.32 (m, 5.60H), 7.07 (d, J=2.7 Hz, 0.33H), 6.68 (m, 1.30H), 5.04 (s, 2H), 4.59 (ss, 2H), 3.96 (br, 1.80), 3.80 (ss, 1.23; H), 3.55 (s, 1.97H), 2.76 (m, 2H).

7-Methoxy-2,3,4,5-tetrahydrobenzo[f][1,4]thiazepine hydrobromide (Amine) (4 HBr salt)

First Method

A solution of HBr (33% in acetic acid, 10 mL) was added to the compound 3 (4.2 g, 12.8 mmol). After the addition, carbon dioxide began to develop and a white solid formed. The mixture was let stand at r.t. for another 2 hours. Diethyl ether (150 mL) was added to the mixture, and it was stirred for 30 min. The solid was collected by filtration and washed with diethyl ether. The solid was dried under vacuum to give the 3.40 g of the target compound with the yield of 91.8%.

$^1$H-NMR (300 MHz, DMSO-$d_6$): 9.02 (br, 2H), 7.52 (d, J=8.1 Hz, 1H), 7.27 (d, J=3.3 Hz, 1H), 6.92 (dd, J=8.4, 2.7 Hz, 1H), 4.41 (s, 2H), 3.77 (s, 3H), 3.53 (m, 2H), 2.96 (m, 2H).

Alternative Method (Free Base 4a)

Compound 3 (10 g, 30 mmol) was mixed with 50 mL of conc. HCl, 50 mL of water and 30 mL of dioxane. The mixture was stirred at 100° C. overnight. After cooling to r.t., most of the solvent and HCl was removed under reduced pressure. Water (100 mL) was added to the solution and the solid was filtered off. The aqueous solution was extracted with EtOAc/hexane (1:1, 3×100 mL) and basified by adding 15 g of NaOH. The mixture was extracted with dichloromethane (3×150 mL). The combined solution was dried over anhydrous sodium sulfate. Removal of solvent provided a liquid that solidified after standing at rt. leaving 6.2 g of target compound.

$^1$H-NMR (300 MHz, CDCl$_3$): 7.42 (d, J=8.1 Hz, 1H), 6.78 (d, J=2.7 Hz, H), 6.68 (dd, J=2.7, 8.1 Hz, 1H), 4.08 (s, 2H), 3.96 (br, 1.80), 3.76 (s, 3H), 3.38 (m, 2H), 2.68 (m, 2H).

Example 2

Binding of Calstabin2 to PKA-phosphorylated RyR2

Cardiac SR membranes were prepared as previously described (Marx et al., 2000; Kaftan et al., Circ. Res., 1996, 78:990-97). Immunoblotting of microsomes (50 μg) was performed as described, with anti-calstabin antibody (1:1,000) (Jayaraman et al., J. Biol. Chem., 1992, 267:9474-77) for 1 hr at room temperature (Reiken et al., Circulation, 107:2459-66, 2003). After incubation with HRP-labeled anti-rabbit IgG (1:5,000 dilution; Transduction Laboratories, Lexington, Ky.), the blots were developed using ECL (Amersham Pharmacia, Piscataway, N.J.) and detected on x-ray film, or exposed to secondary antibodies labeled with infrared Dye and visualized on equipment from Li-Cor Biosciences (model Odyssey). Unless otherwise stated, compounds were tested at a concentration of 100 nM. A representative calstabin2 binding assay is presented below.

A. PKA Phosphorylation of Cardiac Sarcoplasmic Reticulum (CSR)
  B. Reaction mixture was set up in 1.5 ml microfuge tube. 200 μg of cardiac SR were added to a reaction mix of kinase buffer, PKA and ATP to a final volume of 100 μl (Reaction mix below). ATP was added last to initiate the reaction.

Reaction Mix:
20 μl=Sample (cardiac SR, 2 or 10 μg/μl)
10 μl=10× Kinase buffer (80 mM MgCl$_2$, 100 mM EGTA, 500 mM Tris/PIPES),
pH=7.0
20 μl=PKA (2 units/ul) (Sigma #P2645)
10 μl=10×ATP (1.0 mM) (Sigma A 9187)
40 μl=distilled H$_2$O 1. The tubes were incubated at 30° C. for 30 minutes.
2. The reaction mix was then transferred to 0.5 ml thick walled glass tubes.
3. The glass tubes containing the reaction mix were centrifuged for 10 min at 50,000×g in Sorvall Centrifuge RCM120EX using S120AT3 rotor. Centrifugation at 50,000×g for 10 min is sufficient to isolate the microsomes.
4. The resulting pellet was washed 4 times with binding buffer (10 mM Imidazol 300 mM Sucrose, pH=7.4). Each time 100 μl of 1× binding buffer was added to the tube to wash the pellet. The pellet was resuspended by flushing up and down using the pipette tip. After the last spin 50 μl of binding buffer was added and the pellets from all tubes were pooled. The reaction was stored at −20° C.
5. Phosphorylation was confirmed by separating approximately 10 μg of CSR by 6% Polyacylamide gel electrophoresis (PAGE) and analyzing the immunoblots for both total RyR (5029 Ab, 1:3000 dilution or Monoclonal Ab from Affinity Bioreagents, Cat #MA3-916, 1:2000 dilution) and PKA phosphorylated RyR2 (P2809 Ab, 1:10000 dilution).
6. Aliquots can be stored at −80 C.

C. Calstabin Rebinding Assay
1. PKA-phosphorylated CSR (approximately 20 μg) was incubated with 250 nM Calstabin 2 in 100 μl binding buffer (as described above) with or without compounds.
2. The reaction was set up in 0.5 ml thick walled glass tube (Hitachi Centrifuge ware, Catalog #B4105).
3. Calstabin2 was added as the last reagent in the reaction mix. Reaction was carried out at room temperature for 30 mins.
4. After the reaction, the tubes were centrifuged for 10 min at 100,000 g. (Sorvall RCM120EX centrifuge with S120AT3 rotor).
5. The resulting pellet was washed 4 times in 1× binding buffer at 4° C. After each wash the tubes were centrifuged at 50,000 g for 10 mins at 4° C.
6. After the final wash, supernatant was discarded.
7. 20 μl of sample buffer (2×) [6× sample buffer described below] were added and the pellet was resuspended with the tip and/or by brief vortexing. The suspension was transferred to 1.5 ml microcentrifuge tube.
8. The tubes were heated at 90° C. for 4 min.
9. Proteins were separated using 15% SDS/PAGE.
10. Calstabin2 binding was detected with anti-FKBP (Jayaraman et al., J. Biol. Chem. 1992; 267:9474-77, 1:2000) primary antibody and appropriate secondary antibody.

6× Sample Buffer
7.0 ml 4×Tris-HCl/SDS, pH6.8
3.0 ml glycerol (30% final concentration)
1.0 g SDS (10% final concentration)
0.93 g DTT (0.6 M final)
1 mg Bromophenol blue (0.001% final concentration)
Distilled water to 10 ml final volume.
Store in 1 ml aliquots at −70° C.

Results:
FIG. 1A depicts an immunoblot with calstabin2 antibody showing binding of calstabin2 to PKA-phosphorylated RyR2 in the absence (−) or presence of 100 nM compound 1. (+): calstabin binding to non-PKA phosphorylated RyR2. S36, a benzothiazepine described in U.S. Pat. No. 7,544,678, is used as a control. As shown, compound 1, at a concentration of 100 nM, prevented the dissociation of calstabin2 from PKA-phosphorylated RyR2 and/or enhanced the (re)binding of calstabin2 to PKA-phosphorylated RyR.

Figure 1B:
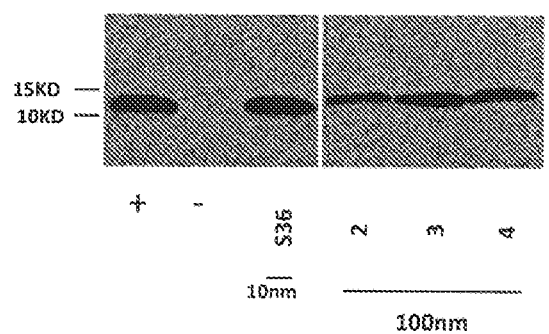
FIG. 1B Immunoblot with calstabin2 antibody showing binding of calstabin2 to PKA-phosphorylated RyR2 in the absence (−) or presence of 100 nM compound 2, compound 3 or compound 4. (+): calstabin binding to non-PKA phosphorylated RyR2. S36 is used as a positive control.

As shown in FIG. 1B, the following representative compounds were also found to prevent dissociation of calstabin2 from PKA-phosphorylated RyR2, and/or enhance the (re) binding of calstabin2 to PKA-phosphorylated RyR2 when tested in the aforementioned calstabin2 rebinding assay at 100 nM: compound 2, compound 3 and compound 4.

Example 3

Binding of Calstabin1 to PKA-Phosphorylated RyR1

SR membranes from skeletal muscle were prepared in a manner similar to Example 2, and as further described in US patent application publication No. 2004/0224368, the contents of which are incorporated by reference herein. Immunoblotting of microsomes (50 μg) was performed as described, with anti-calstabin1 antibody (Zymed) (1:1,000). The blots were developed and quantified as described in Example 2.

Figure 1C:
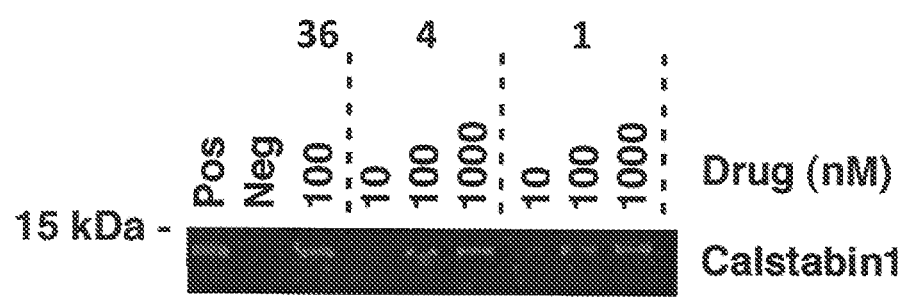
FIG. 1C Immunoblot with calstabin1 antibody showing binding of calstabin1 to PKA-phosphorylated RyR1 in the absence (Neg) or presence of the indicated concentrations of compound 1 or compound 4. (Pos): calstabin binding to non-PKA phosphorylated RyR1. S36 is used as a positive control.

FIG. 1C depicts an immunoblot with calstabin1 antibody showing binding of calstabin1 to PKA phosphorylated RyR1 in the absence (Neg) or presence of the indicated concentrations of compound 1 or compound 4. (Pos): calstabin binding to non-PKA phosphorylated RyR1. S36 is used as a control. As shown, compound 1 and compound 4 prevented the dissociation of calstabin1 from PKA phosphorylated RyR1 and/or enhanced the (re)binding of calstabin1 to PKA-phosphorylated RyR1 in a dose-dependent manner, with an estimated EC50 of about 100 nM and 150 nM, respectively.

Example 4

Calstabin1 Rebinding to RyR1 in Isoproterenol Treated Mice

Isoproterenol, a beta adrenergic receptor agonist, induces heart failure in mice via overstimulation of the beta adrenergic receptor. Concurrent with this is the activation of PKA, phosphorylation of the RyR2 on the SR, and decreased interaction of calstabin2 (FKBP12.6) to RyR2. A similar cascade of events occurs in skeletal muscle, wherein RyR1 is phosphorylated, leading to decreased binding of calstabin1 (FKBP12) to RyR1.

As described in detail in International publication no. WO2008/064264, the contents of which are incorporated by reference herein, chronic isoproterenol treatment to a wild-type mouse offers a fast and reliable method for inducing changes in RyR biochemistry that could be readily quantified. These changes include increased RyR phosphorylation and concomitant decreased calstabin binding.

Animals and Reagents

C57Bl/6 mice were maintained and studied according to approved protocols. The synthetic beta-adrenergic agonist, isoproterenol (ISO) was obtained from Sigma (165627) and prepared as a 100 mg/ml stock in water. Lysis buffer was made by adding sucrose (1 mM), dithiothreitol (320 mM), and 1 protease inhibitor tablet (10×) to 10 ml stock solution (10 mM HEPES, 1 mM EDTA, 20 mM NaF, 2 mM $Na_3VO_4$).

Osmotic Pump Preparation and Surgical Implantation

Mice were continually infused for five days with 10 mg/ml isoproterenol (1 μl/hr) by means of a subcutaneously implanted osmotic infusion pump (Alzet MiniOsmotic pump, Model 2001, Durect Corporation, Cupertino, Calif.).

For drug loading, the osmotic pump was held vertically and 200 μl drug solution was injected into the pump via a 1 ml syringe (attached to a cannula) that contained an excess of drug solution (~250-300 μl). The drug solution was injected slowly downward, while the syringe was slowly lifted, until the pump was overfilled. Overflow of displaced fluid upon capping the pump confirmed that the pump was properly filled.

The loaded osmotic pumps were implanted subcutaneously by the following steps. The recipient mouse was anesthetized with 1.5-2% isoflurane in $O_2$ administered at 0.6 L/min, and its weight was then measured and recorded. The mouse was then placed chest-down on styrofoam, its face in the nose cone. The fur was clipped on the back of the neck, extending behind the ears to the top of the head. The area was wiped gently with 70% alcohol, and a small incision was made at the midline on the nape of head/neck. A suture holder was swabbed with alcohol, inserted into the cut, and opened to release the skin from the underlying tissue. To accommodate the pump, this opening was extended back to the hindquarters. The loaded pump was inserted into the opening, with its release site positioned away from the incision, and was allowed to settle underneath the skin with minimal tension. The incision was closed with 5.0 nylon suture, requiring about 5-6 sutures, and the area was wiped gently with 70% alcohol. Following surgery, mice were placed in individual cages to minimize injury and possible activation of the sympathetic nervous system.

Skeletal Muscle Isolation

Mouse skeletal muscle tissue was isolated as follows. The leg muscles were exposed by cutting the skin at the ankle and pulling upward. The tissue was kept moistened with Tyrode's buffer (10 mM HEPES, 140 mM NaCl, 2.68 mM KCl, 0.42 mM $Na_2HPO_4$, 1.7 mM $MgCl_2$, 11.9 mM $NaHCO_3$, 5 mM glucose, 1.8 mM $CaCl_2$, prepared by adding 20 mg $CaCl_2$ to 100 ml 1× buffer made from a 10× solution without $CaCl_2$).

The following muscles were isolated and frozen in liquid nitrogen. The extensor digitorum longus (EDL) was isolated by inserting scissors between lateral tendon and the X formed by the EDL and Tibialis tendons, cutting upward toward the knee; cutting the fibularis muscle to expose the fan-shaped tendon of gastrocnemius; inserting forceps under X and under the muscle to loosen the EDL tendon; cutting the EDL tendon and pulling up the muscle; and finally cutting loose the EDL. The soleus was isolated by removing the fibularis muscle from top of gastrocnemius; exposing the soleus on the underside of the gastrocnemius by cutting and lifting up the Achilles tendon; cutting the soleus at the top of the muscle behind the knee; and finally pulling the soleus and cutting it away from the gastrocnemius muscle. The tibialis was isolated by cutting the tibialis tendon from the front of ankle, pulling the tendon upwards, and cutting it away from the tibia. The vastus (thigh muscle) was isolated from both legs, by cutting the muscle just above the knee and removing the muscle bundle. The samples were frozen in liquid nitrogen.

RyR1 Immunoprecipitation from Tissue Lysates

RyR1 was immunoprecipitated from samples by incubating 200-500 μg of homogenate with 2 μl anti-RyR1 antibody (Zymed) in 0.5 ml of a modified RIPA buffer (50 mM Tris-HCl (pH 7.4), 0.9% NaCl, 5.0 mM NaF, 1.0 mM Na3VO4, 0.5% Triton-X100, and protease inhibitors) at 4° C. for 1.5 hr. The samples were then incubated with Protein A sepharose beads (Amersham Pharmacia Biotech, Piscatawy, N.J.) at 4° C. for 1 hour, after which the beads were washed three times with ice cold RIPA. Samples were heated to 95° C. and size fractionated by SDS-PAGE (15% SDS-PAGE for calstabin). Immunoblots were developed using an anti-FKBP antibody (FKBP12/12.6, Jayaraman et al., *J. Biol. Chem.* 1992; 267: 9474-77) at a 1:2,000 dilution. The antibodies were diluted in 5% milk or TBS-T (20 mM Tris-HCl, pH 7.5, 0.5 M NaCl, 0.05% Tween® 20, 0.5% Triton X-100).

Results

Osmotic pumps containing isoproterenol with or without test compound were implanted in mice as described above. The mice were osmotically perfused for five days with either vehicle alone (DMSO/PEG), isoproterenol alone (ISO) (0.5 mg/kg/hr), or a combination of isoproterenol (0.5 mg/kg/hr) and compound 1 at the indicated concentrations. At day 6, each mouse was sacrificed, and skeletal muscle tissue was isolated and used to analyze calstabin1 binding in RyR1 immunoprecipates.

Figure 2:
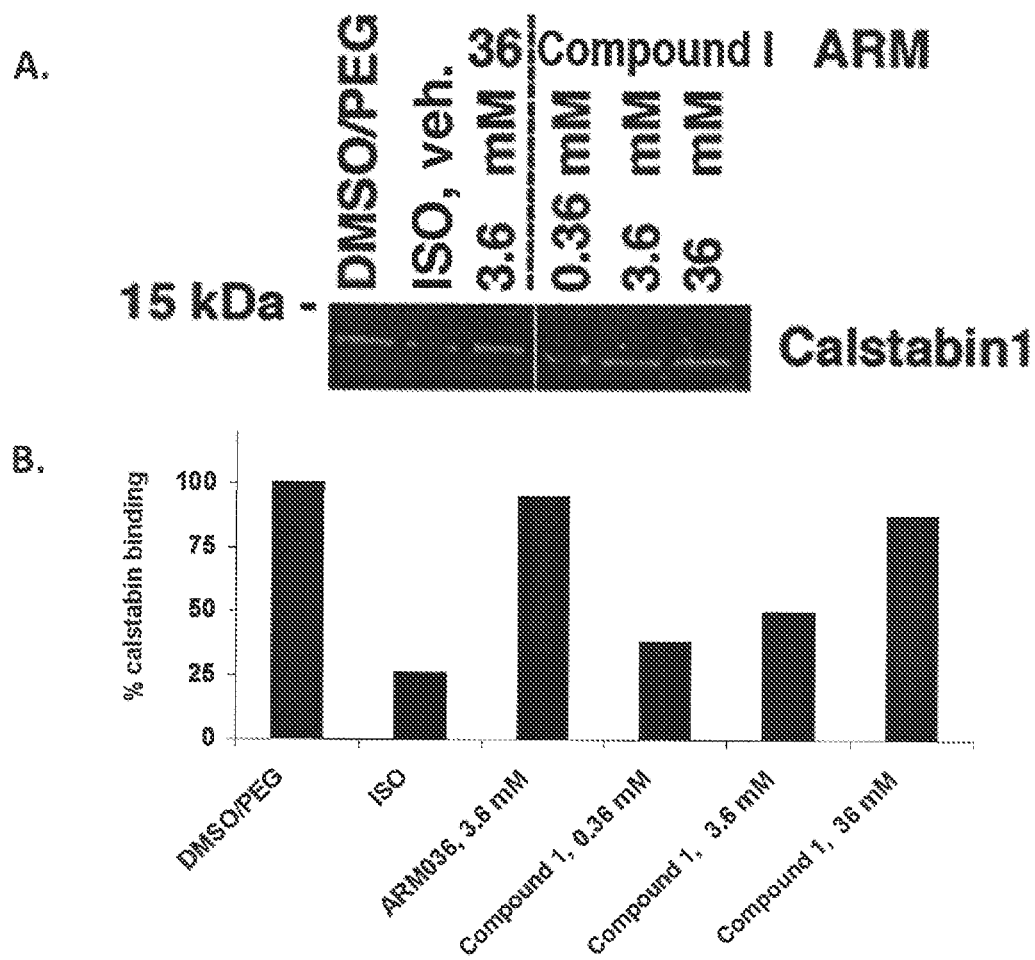
FIG. 2A: Immunoblot with calstabin1 antibody showing the levels of calstabin1 in immunoprecipitated RyR1 complexes from tibialis lysates in mice administered vehicle (50:50 DMSO/PEG), isoproterenol alone (ISO) or isoproterenol together with the indicated concentrations of compound 1 in osmotic pumps. S36 is used as control at 3.6 mM.
FIG. 2B: quantification of % calstabin1 rebinding to RyR1.

The effect of compound 1 on enhancing calstabin1 binding to RyR1 in skeletal muscle isolated from isoproterenol treated mice is depicted in FIGS. 2A (immunoblot) and 2B (graphical quantification). As shown, compound 1 enhanced levels of calstabin1 bound to RyR1 in skeletal muscle membranes to a level similar to that observed by administration of 3.6 mM S36, another benzothiazepine derivative used as a positive control (WO2008/064264). Similar results were obtained for compound 4 (data not shown).

Example 5

Effect of Compound 1 in a Model of Chronic Post-Ischemic Heart Failure in Rat

Objective

The objective of this study was to test the ability of compound 1 to reduce cardiac dysfunction and attenuate ventricular remodelling in a model of ischemia-reperfusion induced heart failure.

Methodology

Figure 3:
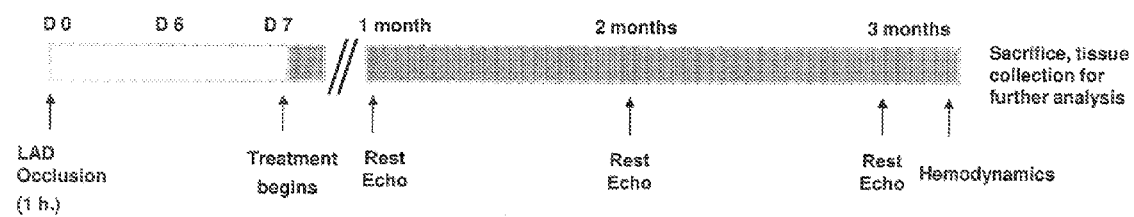
FIG. 3 Rat chronic heart failure model induced by ischemia-reperfusion (I/R) injury. For I/R protocol, the left anterior descending (LAD) coronary artery was occluded for 1 h.

Chronic heart failure was induced in male wistar rats (224-240 g, 10-11 weeks of age) by ischemia-reperfusion (I/R) injury. For I/R protocol, the left anterior descending (LAD) coronary artery was occluded for 1 h. Drug treatment (5 mg/kg/d or 10 mg/kg/d in drinking water) was initiated 1 week after reperfusion and was maintained for a 3 month study period. The efficacy of compound 1 was assessed by echocardiography at one, two and three months after treatment began, and by invasive hemodynamics at 3 months in comparison with vehicle-treated and sham-operated animals. Cardiac specimens were also analyzed to assess hypertrophy and collagen content. Blood was collected from each rat on the final study day to assess drug plasma concentrations as shown in FIG. 3. The study design is depicted in FIG. 3. Experiments were performed in a blinded manner.

Statistical Methods

On parameters measured over time, comparison of Sham versus Vehicle and comparison of drug treatments are analyzed by 2 way ANOVAs with repeated measures. On parameters measured at sacrifice and morphometry, comparisons of Sham versus Vehicle are analyzed by t-test and comparisons of drug treatments by 1-way ANOVA followed by Dunnett test.

Results

Figure 4:
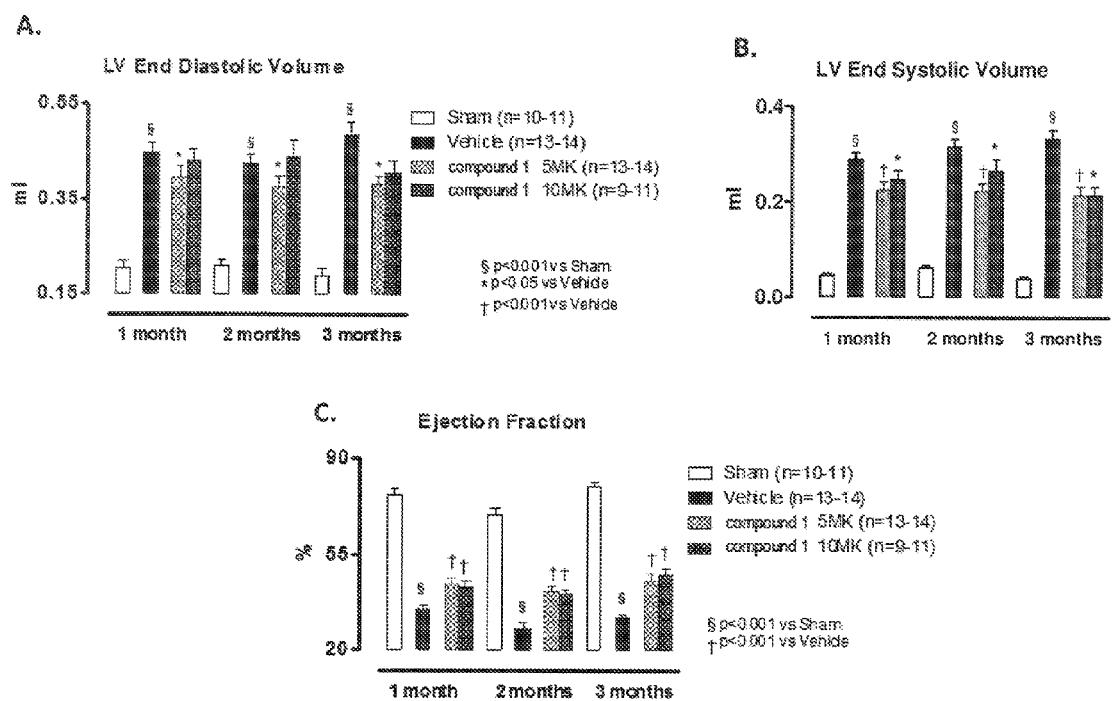
FIG. 4 Left ventricular (LV) volumes and ejection fraction (EF) in rats treated with compound 1 at 5 mg/kg/d (5MK) or 10 mg/kg/d (10MK) in drinking water vs. vehicle ($H_2O$)-treated and sham-operated animals. Chronic heart failure was induced by ischemia-reperfusion (I/R) injury. LAD artery was occluded for 1 h; treatment started 1 week after reperfusion and continued for 3 months. Echocardiographic parameters were obtained after 1, 2 or 3 months of treatment.
Figure 5:
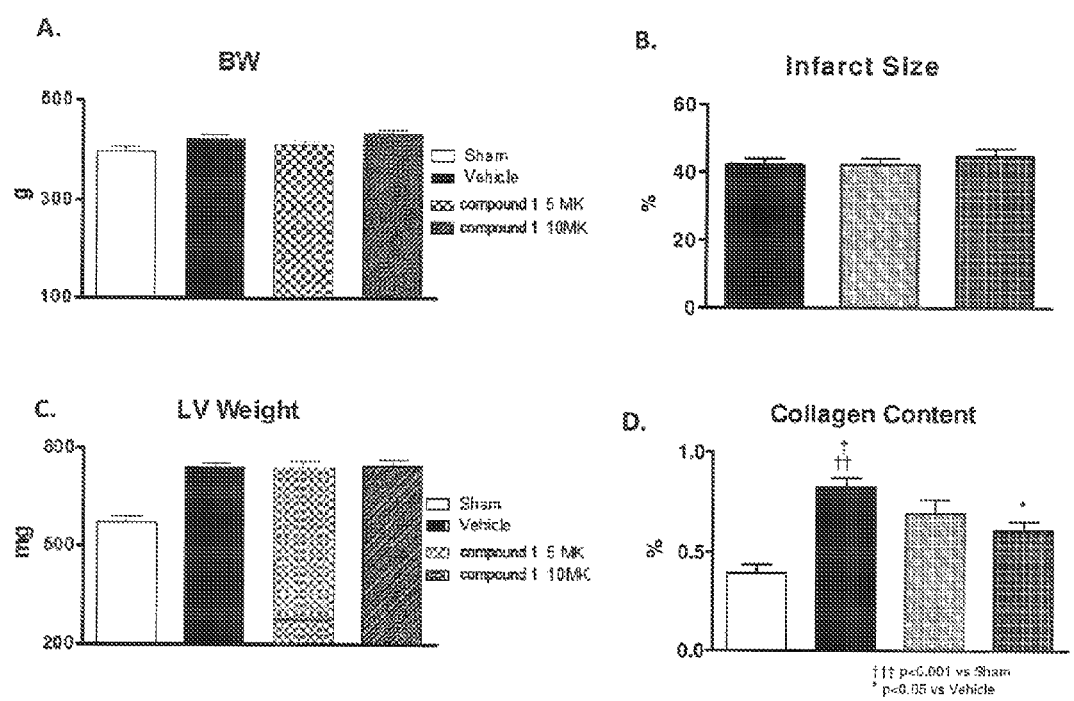
FIGS. 5A-C depict body weight (BW) (5A), Infarct size (5B), and LV weight (5C)
FIG. 5D depicts collagen content in rats treated with compound 1 at 5 mg/kg/d (5MK) and 10 mg/kg/day (10MK) in drinking water vs. vehicle ($H_2O$)-treated and sham-operated animals. Chronic heart failure was induced by ischemia-reperfusion (I/R) injury. LAD artery was occluded for 1 h; treatment started 1 week after reperfusion and continued for 3 months. Parameters were measured after 3 months of treatment.

Vehicle-treated I/R animals, compared to sham-operated animals, showed increased left ventricular (LV) end systolic (LV ESV) and end diastolic (LV EDV) volumes (FIGS. 4 A and B), depressed cardiac function as measured by decreased Ejection Fraction (EF) (FIG. 4C) and increased interstitial collagen content (FIG. 5D). compound 1, administered at 5 and 10 mg/kg/d, significantly increased EF, as well as decreased both LVESV and LVEDV compared to vehicle, from one to three months (FIGS. 4A-C), as well as reduced interstitial collagen content (FIG. 5D).

Figure 6:
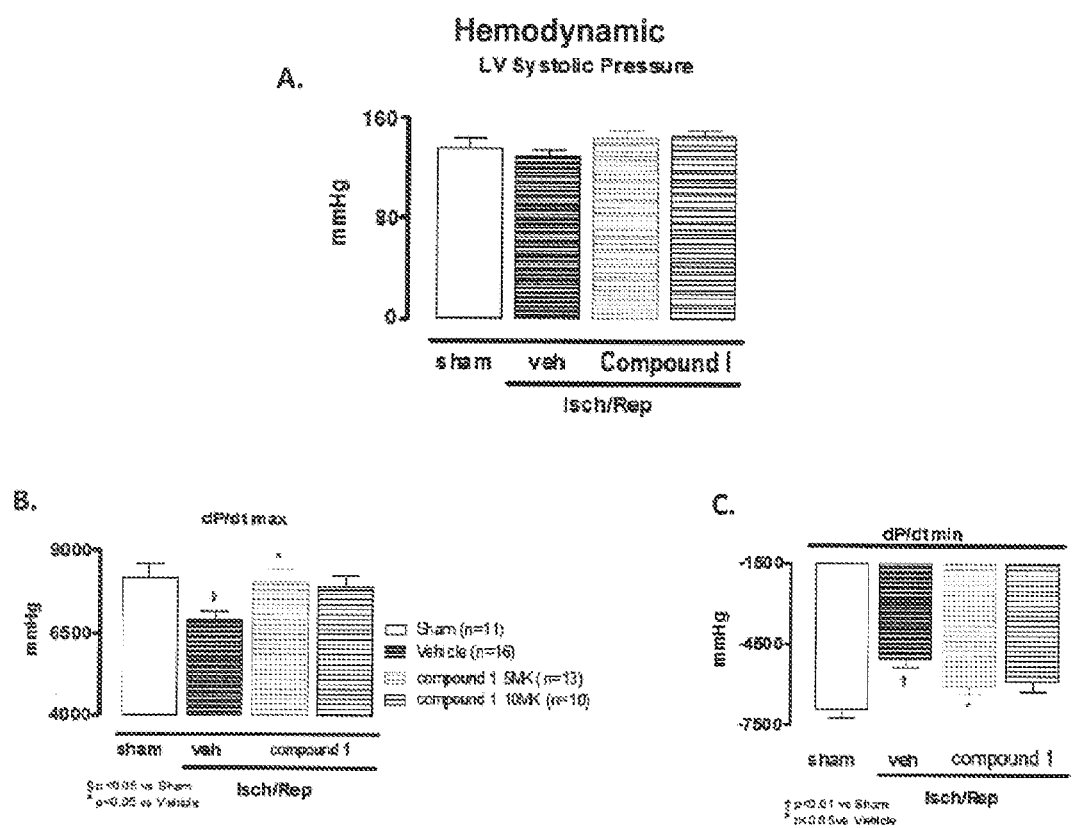
FIG. 6 Invasive hemodynamics: Left ventricular systolic pressure (LV SP) (6A), dP/dtmax (6B); and dP/dtmin (6C) in rats treated with compound 1 at 5 mg/kg/d (5MK) or 10 mg/kg/day (10MK) in drinking water vs. vehicle($H_2O$)-treated and sham-operated animals. Chronic heart failure was induced by ischemia-reperfusion (I/R) injury. LAD artery was occluded for 1 h; treatment started 1 week after reperfusion and continued for 3 months. Hemodynamic parameters were measured after 3 months of treatment.

Invasive hemodynamic study (at 3 months) showed a preservation of LV dP/dt max and LV dP/dt min in the animals treated with compound 1 at 5 and 10 mg/kg/d compared to vehicle (FIGS. 6B and C), with no statistically significant change in LV systolic pressure upon treatment (FIG. 6A).

Figure 7:
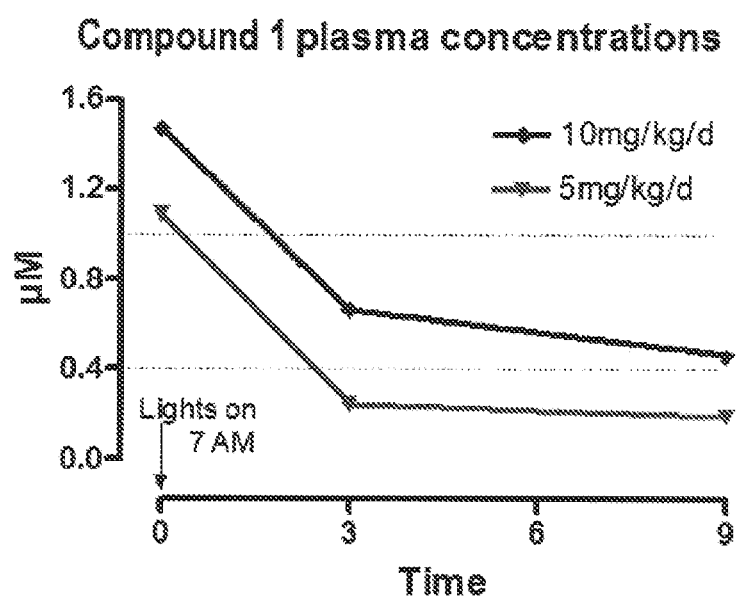
FIG. 7 Compound 1 plasma concentrations (µM) vs. time of day.

No effects on body weight (BW), infarct size or hypertrophy (LV weight) were observed upon treatment (FIGS. 5A-C). Drug plasma concentrations are depicted in FIG. 7.

The results show that compound 1, at concentrations as low as 5 mg/kg/d, exerts a beneficial effect on both systolic and diastolic cardiac function in a model of chronic post-ischemic heart failure in rat.

Figure 8:
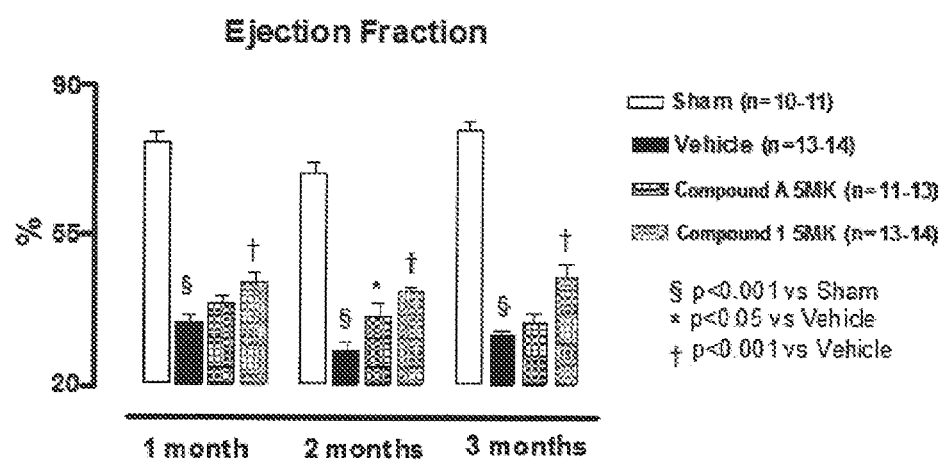
FIG. 8 EF in rats treated with compound 1 or compound A at 5 mg/kg/d (5MK) in drinking water vs. vehicle ($H_2O$)-treated and sham-operated animals. LAD artery was occluded for 1 h; treatment started 1 week after reperfusion and continued for 3 months. Echocardiographic parameters were obtained after 1, 2 or 3 months of treatment. §P<0.001 vs. sham; *P<0.05 vs. vehicle; †P<0.001 vs. vehicle.

Compound 1 was significantly and surprisingly more active in comparison with compound A, a structurally related benzothiazepine derivative described in WO 2007/024717. As shown in FIG. 8, compound A, administered at a concentration of 5 mg/kg/d for 3 months, failed to improve systolic and diastolic cardiac function when compared with compound 1 in the chronic post-ischemic heart failure rat model at the end of the study. Thus, beneficial effects of compound 1, but not compound A, were observed at a dose of 5 mg/kg/d after 3 months of treatment in the rat CHF model.

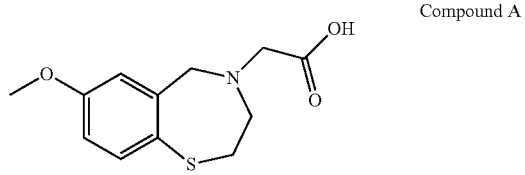 [SMILES: COc1ccc2c(c1)CN(CC(=O)O)CCS2]

Compound A

Example 6

Effect of Compound 1 on Muscle Function in a Mouse Muscular Dystrophy Model (mdx)

Objective

The objective of this study was to test whether treatment with compound 1 improves muscle function in a dystrophin-deficient mouse model (mdx).

Methodology

C57BL/10ScSn-DMD$^{mdx}$/J (abbreviated as mdx, n=5 per group) mice, 6 weeks and approximately 20 grams at study initiation, were acclimated to wheel cages for six days, prior to randomization into groups receiving treatment with either vehicle (H$_2$O) or target doses of 5 mg/kg/d, 10 mg/kg/d, or 50 mg/kg/d (actual doses: 7.9 mg/kg/d; 12.8 mg/kg/d; and 61.5 mg/kg/d, respectively, determined from weekly measured drug solution consumption divided by body weight) of the sodium salt of compound 1 (based on the weight of the parent drug; the sodium salt is referred to hereinafter in this Example as "compound 1") administered in the drinking water ad libitum for 4 weeks. Age-matched C57BL/6 (abbreviated as WT, n=4 per group) mice, were randomized into groups receiving treatment with either vehicle (H$_2$O) or a target dose of 50 mg/kg/d (actual dose: 67.7 mg/kg/d) of the sodium salt of compound 1.

Voluntary activity on wheel, body weight, and average water consumption were measured in the first 3 weeks. Specific muscle force was measured after 4 weeks of treatment, at the end of the study.

Distance traveled (Km/day) over a 24 hr period was analyzed as an index of improved functional activity (see, DMD_M.2.1.002 SOP at http://www.treat-nmd.eu/). At the conclusion of the study, Extensor digitorum longus (EDL) muscle was isolated for muscle force analysis as further described hereinbelow. Blood was collected from each mouse by retro-orbital bleeds at the end of the study (after end of dark cycle—about 7 AM) to assess drug plasma concentrations. Experiments were blinded.

Force Measurements

At the end of the study, EDL muscle was dissected from hind limbs for isometric force analysis using the 407A Muscle Test System from Aurora Scientific (Aurora, Ontario, Canada). A 6-0 suture were tied to each tendon and the entire EDL muscle, tendon to tendon, was transferred to a Ragnoti bath of O$_2$/CO$_2$ (95%/5%) bubbled Tyrode solution (in mM: NaCl 121, KCl 5.0, CaCl$_2$ 1.8, MgCl$_2$, NaH$_2$PO$_4$, NaHCO$_3$ 24, and glucose 5.5). Using the sutures, one tendon was tied vertically to a stainless steel hook connected to a force transducer The other sutured tendon was clamped down into a moving arm on the Aurora system. The EDL muscle was stimulated to contract using an electrical field between two platinum electrodes. At the start of each experiment, muscle length was adjusted to yield the maximum force. Force-frequency relationships were determined by triggering contraction using incremental stimulation frequencies (5-250 Hz for 200 ms at suprathreshold voltage). Between stimulations the muscle was allowed to rest ~3 min. At the end of the force measurement, the length (L$_o$) of the EDL muscle while sutured in the Aurora system was measured excluding the tendons. The EDL muscle was then removed from the system and weighed after clipping the end tendons and sutures off. The EDL muscle was then frozen in liquid nitrogen. The cross-sectional area (mm$^2$) of the EDL muscle was calculated by dividing the EDL muscle weight by the EDL muscle length and the mammalian muscle density constant of 1.056 mg/m$^3$ (Yamada, T., et al. *Arthritis and rheumatism* 60:3280-3289). To determine EDL specific force (kN/m$^2$), the absolute tetanic force was divided by the EDL muscle cross-sectional area.

Statistical Methods

For statistical analysis of distance traveled, change from baseline was calculated for each day by subtracting the baseline value (defined as the mean of the two measurements obtained on Day −1 and Day −2) from each post dose assessment. Change from baseline was then statistically analyzed with a repeated measures analysis of variance model with fixed effects for treatment, day and treatment by day interaction. Baseline was included as a covariate and mouse was included as a random effect. The most appropriate covariance structure was determined through investigation of the Akaike's Information Criterion (AIC) and Bayesian Information Criterion (BIC). The covariance structures investigated were autoregressive, compound symmetry, unstructured, and toeplitz. The optimal covariance structure selected was compound symmetry. From the model, point estimates and associated 95% confidence intervals (CI) for the difference in change from baseline between each ARM210 treated mice group and vehicle treated group (for both mdx and C57BL/6 mice) were obtained for each day, each week, and the entire assessment period from Day 1 to Day 19. As this study is exploratory in nature, no adjustments in multiple comparisons were made.

Specific force was analyzed using a repeated measures analysis of variance model with fixed effects for treatment, frequency and treatment by frequency interaction and mouse as a random effect. Similar to the analysis described above, the optimal covariance structure was chosen from among autoregressive, compound symmetry, unstructured, and toeplitz. The optimal covariance structure selected for specific force was toeplitz. From the model, point estimates and associated 95% confidence intervals (CI) for the difference in specific force between each ARM210 treated mice group and vehicle treated group (for both mdx and C57BL/6 mice) were obtained for each frequency and across all frequencies. As this study is exploratory in nature, no adjustments in multiple comparisons were made.

Results

Figure 9:
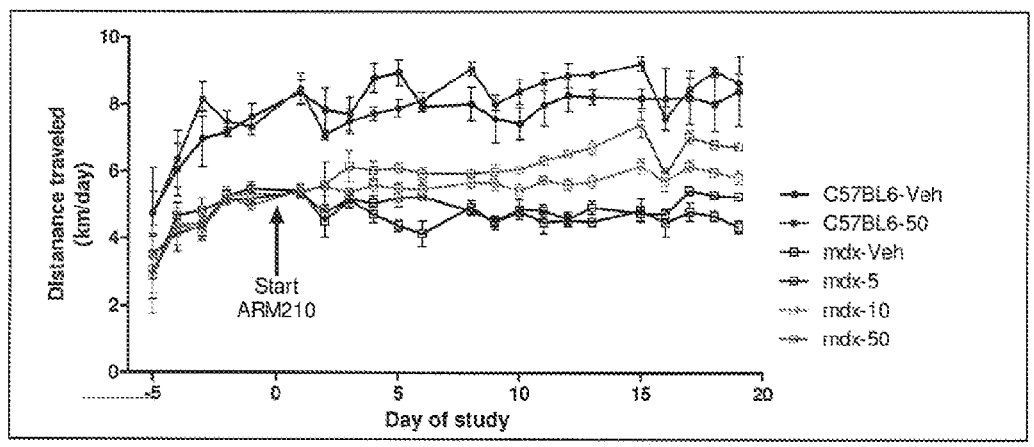
FIG. 9 Effect of compound 1 on spontaneous physical activity of mdx and WT mice as compared with vehicle ($H_2O$)-treated controls. P<0.001 for days 1-19 activity in mdx mice dosed with 10 and 50 mg/kg/day (target dose) administered in drinking water, compared to vehicle control.
Figure 10:
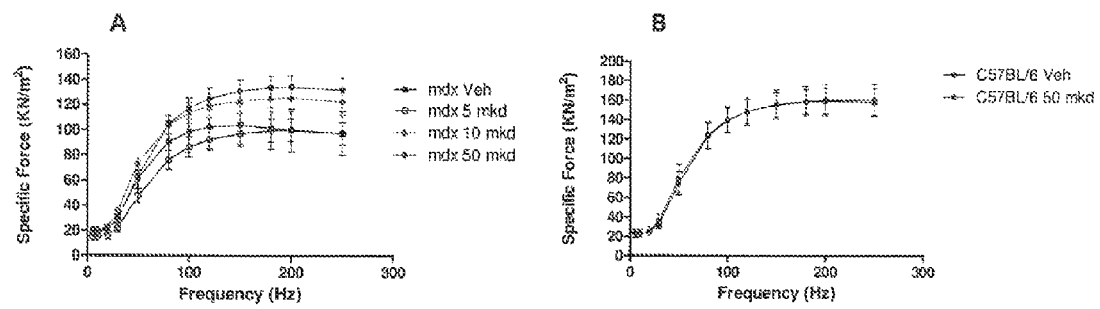
FIG. 10 Specific force-frequency relationship of EDL muscle. (A) mdx mice treated with compound 1 (5, 10 and 50 mg/kg/d (target dose)) administered in drinking water, as compared with vehicle ($H_2O$)-treated controls (n=5). p<0.05, for the 50 mg/kg/d dose, at frequencies of 150 Hz and above. (B) WT, C57BL/6, mice treated with compound 1 (50 mg/kg/d (target dose) administered in drinking water, as compared with vehicle ($H_2O$)-treated controls (n=4).

The ability of compound 1 to improve voluntary exercise in mdx mice was tested. After acclimating the mice to the voluntary wheel cage, mouse activity on the voluntary wheels was monitored by a computer 24/7. Data collected was transcribed to distance traveled per day over 3 weeks. Mdx mice treated with 10 and 50 mg/kg/d (target dose) of compound 1 traveled significantly longer distances on the wheel compared to mdx mice treated with vehicle ($H_2O$) alone (P<0.001 from day 1 to day 19). Treatment effect observed as early as 2-3 days after treatment initiation, and continued throughout the activity monitoring period. No effect of compound 1 on travel distance was observed with WT mice treated with 50 mg/kg/d compound 1 (FIG. 9). In addition, as determined by in vitro force measurements in EDL muscle (FIG. 10), compound 1 treatment increased specific force in mdx muscle dose-dependently. At stimulation frequencies of 150 Hz and above the 50 mg/kg/d-treated mdx mice showed statistically significant increase in specific muscle force (P<0.05). No effect of compound 1 treatment on specific muscle force was observed in WT mice.

Figure 11:
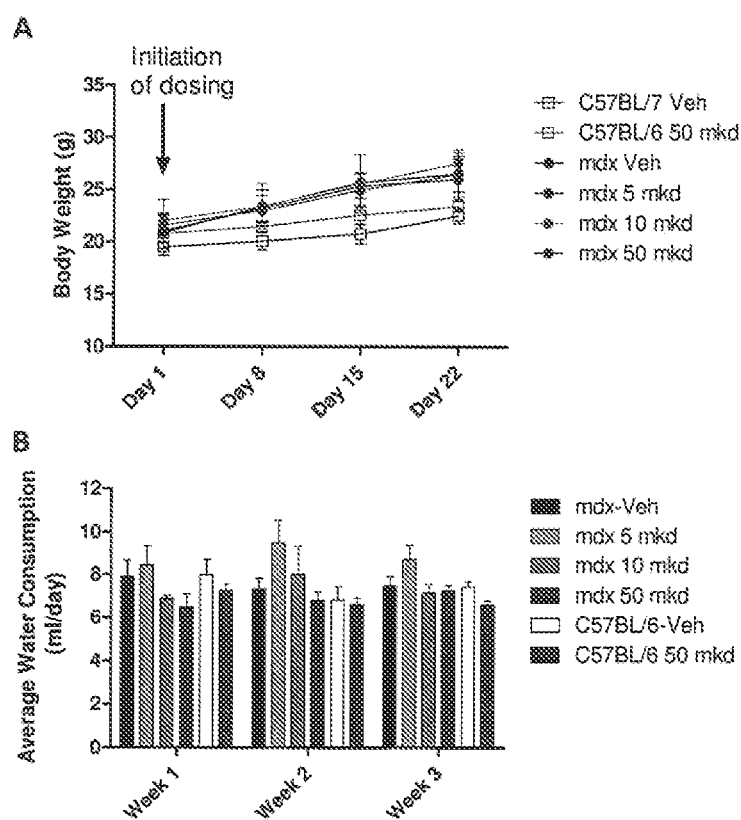
FIG. 11 Average body weight (11A) and average water consumption (11B) of mdx and WT mice treated with vehicle ($H_2O$) or compound 1 administered in drinking water.

As shown in FIG. 11, compound 1 treatment did not affect body weight. No dose-dependent effects on water consumption were observed. Morning blood exposure of compound 1 was (average±SEM) 3.3±0.4 μM for the 5 mg/kg/d-dosed mdx mice, 10.7±0.9 μM for the 10 mg/kg/d-dosed mdx mice, 52.8±1.7 μM for the 50 mg/kg/d-dosed mdx mice and 72.8±7.0 μM for the 50 mg/kg/d-dosed WT mice.

Taken together, the results show that, as compared with vehicle-treated controls, treatment with compound 1 at 10 mg/kg/d and 50 mg/kg/d (target dose) improved voluntary wheel exercise after 3 weeks and specific muscle force after 4 weeks in mdx mice, a murine model of Duchenne muscular dystrophy (DMD), thereby demonstrating the utility of compound 1 and its analogs as claimed herein, in the treatment of muscular dystrophy.

Example 7

Metabolic Stability

The metabolic stability of compound 1, a representative Rycal™ according to the present invention, was compared to compound B and compound C, structurally related benzothiazepine derivative described in WO 2007/024717.

A. Metabolic Stability in Human Hepatic Microsomes

Methods:

Compound solubilization: Stock solutions were made in DMSO, and working solutions in water containing 1 mg/ml BSA.

Prediction of metabolic bioavailability: Metabolic bioavailability predictions (MF %) were based on in vitro metabolic stability measurements with hepatic microsomes assuming total absorption. Briefly, unchanged drugs were quantified by LC-MS-MS following incubation ($10^{-7}$M) with rat and human hepatic microsomes (0.33 mg protein/ml) after 0, 5, 15, 30 and 60 min of incubation in presence of NADPH (1 mM). Enzymatic reaction was stopped with methanol (v/v) and proteins were precipitated by centrifugation. The in vitro intrinsic clearances (Clint_mic) expressed as ml/min/g protein were the slope (after LN linearization) of the unchanged drug remaining concentration versus incubation time. In vitro Clint were then scaled up to in vivo whole body (vivoClint) using 0.045 mg prot/kg of liver and liver weight of 11 g for the rat and 1.2 kg for Man. In vivo Clint were then transformed into hepatic clearances (HepCl) using the well-stirred model (HepCl=vivoClint*HBF/(vivoClint+HBF) where HBF (hepatic blood flow) were taken as 22 ml/min for the rat and 1500 ml/min for Man. The MF % were then deducted from the extraction ratio with the following equation (MF %=1-HepCl/HBF). The results are presented in Table 1:

TABLE 1

Stability in human microsomes

| Compound | Structure | Rat microsomes | | | Human microsomes | | |
|---|---|---|---|---|---|---|---|
| | | Clint_mic rat ml/min/ gprot | MF mic % | Class | Clint_mic man ml/min/ gprot | MF mic % | Class |
| B | 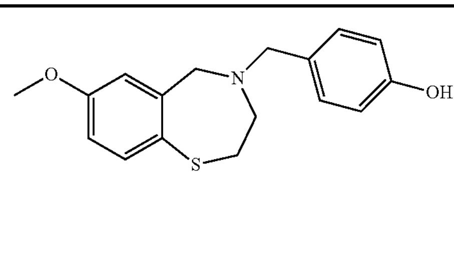 | 823 | 5 | very low | 285 | 6 | very low |

TABLE 1-continued

| | | Rat microsomes | | | Human microsomes | | |
|---|---|---|---|---|---|---|---|
| Compound | Structure | Clint_mic rat ml/min/ gprot | MF mic % | Class | Clint_mic man ml/min/ gprot | MF mic % | Class |
| C | 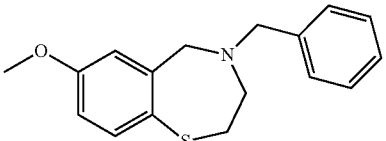 | 1926 | 2 | very low | 1326 | 2 | very low |
| 1 | 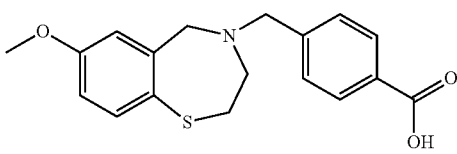 [SMILES: COc1ccc2c(c1)CN(Cc1ccc(C(=O)O)cc1)CCS2] | 101 | 30 | Intermediate | 9.1 | 75 | high | a. Clint_mic: in vitro intrinsic clearance in ml/min/g protein
b. MF %: metabolic bioavailability in %

B. Metabolic Stability in Rat and Human Hepatic Hepatocytes

Compound solubilization: Stock solutions were made in DMSO, and working solutions in William medium containing 1/10 rat plasma or 1/4 human plasma.

Metabolic stability determination: Compounds were incubated at $10^{-7}$ M with isolated hepatocytes (6E+5 cells/ml for rat hepatocytes and 4E+5 cells/ml for human hepatocytes) at 37° C. in plasma from the same species diluted in Wiliams medium (1/10 dilution for rat and 1/4 dilution for human). Sampling times were performed at 0, 10, 20, 30, 60 and 120 min and enzymatic reaction stopped with methanol (v/v). Proteins were precipitated by centrifugation and the supernatant was analyzed by LC/MS/MS. Clint expressed as ml/min/g protein were calculated as for hepatic microsomes using a ratio of 0.134 mg protein/ml for 4E+5 cells/ml for human and 0.201 mg protein/ml for 6E+5 cells/ml for rat. The presence of the reference drug and the potential metabolite was checked by LC/MS/MS during the assay in each sample. The results are presented in Table 2:

TABLE 2

Stability in rat and human hepatocytes

| | Rat hepatocytes | | | Human hepatocytes | | |
|---|---|---|---|---|---|---|
| Compound | Clint (ml/min/ gprot) | MF rat % | Q cellules/ ml | Clint (ml/min/ gprot) | MF human % | Q cellules/ ml |
| B | 1334 | 3 | 6.00E+05 | 693 | 3 | 4.00E+05 |
| 1 | 5 | 90 | 6.00E+05 | 0 | 100 | 4.00E+05 |
| C | 2610 | 2 | 6.00E+05 | 100 | 16 | 4.00E+05 | a. Clint_mic: in vitro intrinsic clearance in ml/min/gprotein
b. MF %: metabolic bioavailability in %
c. Q: cells quantity per ml C. Metabolic Stability in Mouse and Rat Microsomes
Materials and Methods Dilution Buffer: 0.1M Tris HCl buffer at pH 7.4 containing 5 mM EDTA.

NADPH Cofactor Solution: To a 50 mL falcon tube containing 2.79 mL of dilution buffer were added 0.429 mL of NADPH-regenerating soln. A and 0.079 mL of NADPH-regenerating soln. B Microsome Preparation: (1.5 mg/mL solution) A 50 mL falcon tube containing 3.32 mL of dilution buffer was prewarmed at 37° C. for 15 min. (at least 10 min.) 0.178 mL of microsome (24.6 mg/mL) were added to the prewarmed dilution buffer. The protein concentration of this microsome preparation was 1.25 mg/mL.

Sample (Test Compound)—Original and Intermediate Stock Solutions: A 1 mg/mL (0.5 mg/mL was used for compound 1) solution of the test compound in methanol was prepared. 100 µM intermediate solution of the test compound from the original stock solution were prepared using the dilution buffer. A 5 µM solution was prepared by diluting the 100 µM intermediate solution using dilution buffer.

Experiment:
(The experiments were conducted in 1.5 mL eppendorf micro centrifuge tubes)

0 Minutes Incubation. Procedure:
a. Add 100 µL of prewarmed microsomes
b. Add 50 µL of 5 µM solution of the test compound.
c. Add 500 µL of cold stop solution (ice cold Methanol)
d. Add 100 µL of NADPH cofactor solution to the eppendorf.
a. Vortex mix the eppendorf.

"t" Minutes Incubation
b. Add 100 µL of NADPH cofactor solution to the eppendorf.
c. Add 50 µL of 5 µM solution of the test compound.
d. Add 100 µL of prewarmed microsomes
e. Incubate the eppendorf at 37° C. 300 rpm for 't' min. on a thermomixer.
f. Remove the eppendorf from thermomixer
g. Add 500 µL of cold stop solution (ice cold Methanol)
h. Vortex mix the eppendorf.

Both the '0' and T minutes incubated samples were centrifuged at 15,000 rcf at 4° C. for 15 min. 500 µL of the supernatant solution was removed and subject it to LC/MS analysis (SIM—Selected Ion Monitoring)

Results are expressed as % test compound remaining=(MS Area response of T min sample/MS Area response of '0' min sample)*100. The MS area used is an average of duplicate injections.

Time points=0, 15, 30 and 60 min. for each test compound

Positive Control:

2 µM Imipramine—5 min. and 2 µM Imipramine—15 min. incubation was used as a positive control for the rat and mouse liver microsome stability experiments.

The results are presented in Table 3:

TABLE 3

Stability in mouse and rat microsomes

| In Vitro Metabolic Stability | Compound (1) | Compound (B) | Compound (C) |
|---|---|---|---|
| Rat microsomes (% remaining) | | | |
| 15 min | 54% | 1% | 0% |
| 30 min | 17% | 0% | 0% |
| 1 h | 2% | 0% | 0% |
| Mouse microsomes (% remaining) | | | |
| 15 min | 99% | 0% | 0% |
| 30 min | 98% | 0% | 0% |
| 1 h | 82% | 0% | 0% |

Surprisingly, as seen in Tables 1-3, compound 1 was significantly more stable in mouse, rat and human microsomes, and in rat and human hepatocytes, as compared with the structural analogs compounds B and C disclosed in WO 2007/024717, both of which have been found to possess poor in-vitro metabolic stability in the tested systems, making these compounds unsuitable for development as drug candidates. Surprisingly and unexpectedly, the replacement of the H or OH moieties in the prior art compounds with a COOH moiety resulted in compound 1, which displayed high metabolic stability in all tested systems. The increased metabolic stability of Compound 1 compared with its structural analogs was indeed surprising and substantiates the unexpected benefits of this compound over compounds known in the art.

All publications, references, patents and patent applications cited herein are incorporated by reference in their entirety to the same extent as if each individual application, patent or patent application was specifically and individually indicated to be incorporated by reference in its entirety.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of illustration and not of limitation. The means, materials, and steps for carrying out various disclosed functions may take a variety of alternative forms without departing from the invention.

What is claimed is:

1. A compound represented by the structure of Formula (I):

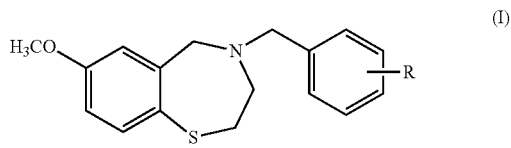

(I)

wherein

R is COOH;

and pharmaceutically acceptable salts thereof.

2. The compound according to claim 1, in the form of a salt with a pharmaceutically acceptable acid or base.

3. The compound according to claim 2, wherein the salt is selected from the group consisting of sodium, potassium, magnesium, hemifumarate, hydrochloride and hydrobromide.

4. The compound according to claim 3, wherein the salt is the sodium or the hemifumarate salt.

5. The compound according to claim 1, which is selected from the group consisting of:

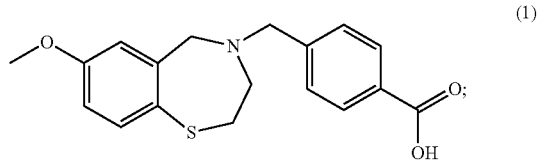

(1)

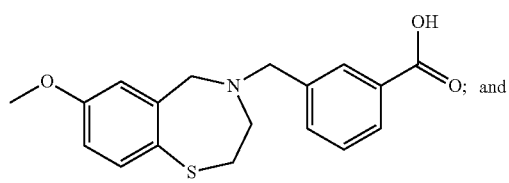

(4)

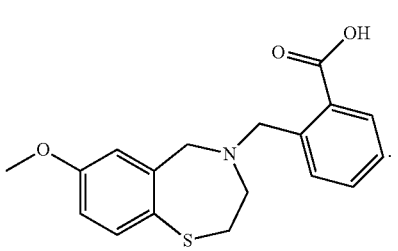

(6)

6. The compound according to claim 1, which is represented by the structure of Formula (1):

SEQUENCE LISTING

<160> NUMBER OF SEQ ID NOS: 1

<210> SEQ ID NO 1
<211> LENGTH: 25
<212> TYPE: DNA
<213> ORGANISM: Artificial Sequence
<220> FEATURE:
<223> OTHER INFORMATION: Synthesized nucleic acid

<400> SEQUENCE: 1
ggccaaacct cggcttacct gaaat                                25

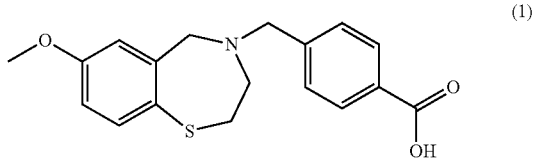 [SMILES: COc1ccc2c(c1)CN(Cc1ccc(C(=O)O)cc1)CCS2]

(1)

or pharmaceutically acceptable salts thereof.

7. The compound according to claim 6, in the form of a salt with a pharmaceutically acceptable acid or base.

8. The compound according to claim 7, wherein the salt is selected from the group consisting of sodium, potassium, magnesium, hemifumarate, hydrochloride and hydrobromide.

9. The compound according to claim 8, wherein the salt is the sodium salt.

10. The compound according to claim 8, wherein the salt is the hemifumarate salt.

11. A pharmaceutical composition comprising a compound according to claim 1, in combination with one or more pharmaceutically acceptable excipients or carriers.

12. A method of treating a condition selected from the group consisting of cardiac disorders and diseases, muscle fatigue, musculoskeletal disorders and diseases; CNS disorders and diseases, cognitive dysfunction, neuromuscular disorders and diseases, bone disorders and diseases, cancer cachexia, malignant hyperthermia, diabetes, sudden cardiac death, and sudden infant death syndrome, or for improving cognitive function, the method comprising the step of administering to a subject in need thereof a therapeutically effective amount of a compound according to claim 1 or a pharmaceutical composition comprising such compound, to effectuate such treatment;

wherein the cardiac disorders and diseases are selected from the group consisting of irregular heartbeat disorders and diseases, exercise-induced irregular heartbeat disorders and diseases, heart failure, congestive heart failure, chronic heart failure, acute heart failure, systolic heart failure, diastolic heart failure, acute decompensated heart failure, cardiac ischemia/reperfusion (I/R) injury, chronic obstructive pulmonary disease, I/R injury following coronary angioplasty or following thrombolysis for the treatment of myocardial infarction (MI); and high blood pressure;

wherein the musculoskeletal disorders or diseases are selected from the group consisting of exercise-induced skeletal muscle fatigue, a congenital myopathy, muscular dystrophy, spinal muscular atrophy (SMA), spinal and bulbar muscular atrophy (SBMA), age-related muscle fatigue, sarcopenia, central core disease, cancer cachexia, bladder disorders, and incontinence:

wherein the muscle fatigue is due to a skeletal muscle disease, disorder or condition;

wherein, the CNS disorders and diseases are selected from the group consisting of Alzheimer's Disease (AD), neuropathy, seizures, Parkinson's Disease (PD), and Huntington's Disease (HD); and the neuromuscular disorders and diseases are selected from the group consisting of spinocerebellar ataxia (SCA), and Amyotrophic lateral sclerosis (ALS, Lou Gehrig's disease);

wherein the cognitive dysfunction is stress-related or age-related, or wherein the cognitive function to be improved is short term memory, long term memory, attention or learning, or wherein the cognitive dysfunction is associated with a disease or disorder selected from the group consisting of Alzheimer's disease (AD), attention deficit hyperactivity disorder (ADHD), autism spectrum disorder (ASD), generalized anxiety disorder (GAD), obsessive compulsive disorder (OCD), Parkinson's Disease (PD), post-traumatic stress disorder (PTSD), Schizophrenia, Bipolar disorder, and major depression.

13. The method according to claim 12, wherein the condition is associated with an abnormal function of a ryanodine receptor 1 (RyR1), a ryanodine receptor type (RyR2), a ryanodine receptor type 3 (RyR3), or a combination thereof.

14. The method according to claim 12, wherein the compound is administered to a subject to treat cardiac disorders and diseases selected from the group consisting of irregular heartbeat disorders and diseases, exercise-induced irregular heartbeat disorders and diseases, heart failure, congestive heart failure, chronic heart failure, acute heart failure, systolic heart failure, diastolic heart failure, acute decompensated heart failure, cardiac ischemia/reperfusion (I/R) injury, chronic obstructive pulmonary disease, I/R injury following coronary angioplasty or following thrombolysis for the treatment of myocardial infarction (MI); and high blood pressure.

15. The method according to claim 12, wherein the irregular heartbeat disorders and diseases are selected from the group consisting of atrial and ventricular arrhythmia, atrial and ventricular fibrillation, atrial and ventricular tachyarrhythmia, atrial and ventricular tachycardia, catecholaminergic polymorphic ventricular tachycardia (CPVT), and exercise-induced variants thereof.

16. The method according to claim 12, wherein the compound is administered to a subject to treat muscle fatigue that is due to a skeletal muscle disease, disorder or condition.

17. The method according to claim 12, wherein the compound is administered to a subject to treat a musculoskeletal disorder or disease selected from the group consisting of exercise-induced skeletal muscle fatigue, a congenital myopathy, muscular dystrophy, spinal muscular atrophy (SMA), Spinal and bulbar muscular atrophy (SBMA), age-related muscle fatigue, sarcopenia, central core disease, cancer cachexia, bladder disorders, and incontinence.

18. The method according to claim 12, wherein the muscular dystrophy is selected from the group consisting of Duchenne Muscular Dystrophy (DMD), Becker's Muscular Dystrophy (BMD), Limb-Girdle Muscular Dystrophy (LGMD), facioscapulohumeral dystrophy, myotonic muscular dystrophy, congenital muscular dystrophy (CMD), distal muscular dystrophy, Emery-Dreifuss muscular dystrophy, and oculopharyngeal muscular dystrophy.

19. The method according to claim 12, wherein the compound is administered to a subject to treat CNS disorders and diseases selected from the group consisting of Alzheimer's Disease (AD), neuropathy, seizures, Parkinson's Disease (PD), and Huntington's Disease (HD); and the neuromuscular disorders and diseases are selected from the group consisting of Spinocerebellar ataxia (SCA), and Amyotrophic lateral sclerosis (ALS, Lou Gehrig's disease).

20. The method according to claim 12, wherein the compound is administered to a subject to treat cognitive dysfunction that is stress-related or age-related, or to improve cognitive function selected from short term memory, long term memory, attention and learning, or wherein compound is administered to a subject to treat cognitive dysfunction associated with a disease or disorder selected from the group consisting of Alzheimer's disease (AD), attention deficit hyperactivity disorder (ADHD), autism spectrum disorder (ASD), generalized anxiety disorder (GAD), obsessive compulsive disorder (OCD), Parkinson's Disease (PD), post-traumatic stress disorder (PTSD), Schizophrenia, Bipolar disorder, and major depression.

21. The method according to claim 12, wherein the condition is cancer cachexia.

22. The method according to claim 12, wherein the compound is used at a dose sufficient to restore or enhance binding of calstabin2 to RyR2.

23. The method according to claim 12, wherein the compound is used at a dose sufficient to restore or enhance binding of calstabin1 to RyR1.

24. The method according to claim 12, wherein the compound is used at a dose sufficient to decrease $Ca^{2+}$ leak through a RyR channel.

25. The method according to claim 12, further comprising the use of an antisense oligonucleotide (AO) which is specific for a splicing sequence in an mRNA of interest, for enhancing exon skipping in said mRNA of interest.

26. A method for treating a subject that has Duchenne Muscular Dystrophy (DMD), comprising the step of administering to said subject a compound according to claim 1, or a pharmaceutical composition comprising such compound, in combination with an antisense oligonucleotide (AO) which is specific for a splicing sequence of at least one exon of the DMD gene.

27. A process for the preparation of a compound according to claim 1, comprising the step of reacting a compounds of the formula

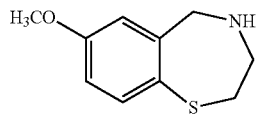

with a compound of the formula

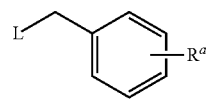

wherein $R^a$ is $COOR^1$ or CN; $R^1$ is a $C_1$-$C_4$ alkyl, and L is a leaving group to afford a compound of the formula:

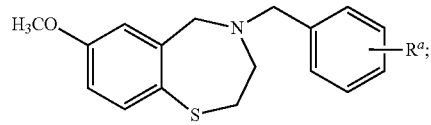

and converting the group $R^3$ to the group R so as to afford a compound of formula (I).

28. The method according to claim 21, wherein the cancer cachexia is due to a cancer having hone metastases.

29. The method according to claim 26, wherein the AO is specific for a splicing sequence of exon 23, 45, 44, 50, 51 52 and/or 53 of the DMD gene.

* * * * *

UNITED STATES PATENT AND TRADEMARK OFFICE
CERTIFICATE OF CORRECTION

| | | |
|---|---|---|
| PATENT NO. | : 8,853,198 B2 | Page 1 of 1 |
| APPLICATION NO. | : 14/076474 | |
| DATED | : October 7, 2014 | |
| INVENTOR(S) | : Jiaming Yan et al. | |

It is certified that error appears in the above-identified patent and that said Letters Patent is hereby corrected as shown below:

Title page, item (72) insert -- ; Andrew R. Marks, Larchmont, NY (US); Jean-Louis Peglion, Le Vesinet (FR) --.

Signed and Sealed this
Eighth Day of March, 2016

Michelle K. Lee
*Director of the United States Patent and Trademark Office*